(12) United States Patent
Garrait et al.

(10) Patent No.: US 10,919,824 B2
(45) Date of Patent: Feb. 16, 2021

(54) COMPOSITIONS OF CHROMIUM OXYFLUORIDE OR FLUORIDE CATALYSTS, THEIR PREPARATION AND THEIR USE IN GAS-PHASE PROCESSES

(71) Applicant: Arkema France, Colombes (FR)

(72) Inventors: Dominique Garrait, Charly (FR); Anne Pigamo, Francheville (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/324,806

(22) PCT Filed: Aug. 28, 2017

(86) PCT No.: PCT/FR2017/052286
§ 371 (c)(1),
(2) Date: Feb. 11, 2019

(87) PCT Pub. No.: WO2018/042114
PCT Pub. Date: Mar. 8, 2018

(65) Prior Publication Data
US 2019/0169102 A1 Jun. 6, 2019

(30) Foreign Application Priority Data

Aug. 29, 2016 (FR) ...................... 1657989

(51) Int. Cl.
*C07C 17/20* (2006.01)
*B01J 27/12* (2006.01)
(Continued)

(52) U.S. Cl.
CPC ............ *C07C 17/358* (2013.01); *B01J 27/12* (2013.01); *B01J 27/128* (2013.01); *B01J 27/132* (2013.01);
(Continued)

(58) Field of Classification Search
None
See application file for complete search history.

(56) References Cited

U.S. PATENT DOCUMENTS

| 5,741,748 A | 4/1998 | Allen et al. |
| 2013/0035526 A1* | 2/2013 | Elsheikh ................. C07C 17/25 570/156 |
| 2015/0360218 A1 | 12/2015 | Syvret et al. |

FOREIGN PATENT DOCUMENTS

| EP | 0 502 605 A1 | 9/1992 |
| EP | 2223906 A1 | 9/2010 |

(Continued)

OTHER PUBLICATIONS

International Search Report (PCT/ISA/210) dated Nov. 15, 2017, by the European Patent Office as the International Searching Authority for International Application No. PCT/FR2017/052286.
(Continued)

*Primary Examiner* — Medhanit W Bahta
(74) *Attorney, Agent, or Firm* — Buchanan Ingersoll & Rooney P.C.

(57) ABSTRACT

The present invention relates to a process for modifying the fluorine distribution in a hydrocarbon compound in the presence of a catalyst, characterized by the use, as catalyst, of a solid composition comprising at least one component containing chromium oxyfluoride or fluoride of empirical formula $Cr_xM_{(1-x)}O_rF_s$, where $2r+s$ is greater than or equal to 2.9 and less than 6, M is a metal chosen from columns 2 to 12 of the Periodic Table of the Elements, x has a value from 0.9 to 1, s is greater than 0 and less than or equal to 6 and r is greater than or equal to 0 and less than 3, the said solid composition having a crystallinity of less than 20% by weight. The present invention also relates to the solid composition per se.

9 Claims, 1 Drawing Sheet

(51) Int. Cl.
| | |
|---|---|
| *B01J 27/128* | (2006.01) |
| *B01J 27/132* | (2006.01) |
| *C07C 17/358* | (2006.01) |
| *B01J 37/26* | (2006.01) |
| *B01J 38/12* | (2006.01) |
| *B01J 27/138* | (2006.01) |
| *B01J 27/32* | (2006.01) |
| *B01J 35/10* | (2006.01) |
| *C07C 17/25* | (2006.01) |
| *B01J 35/00* | (2006.01) |

(52) U.S. Cl.
    CPC ............ *B01J 27/138* (2013.01); *B01J 27/32* (2013.01); *B01J 35/002* (2013.01); *B01J 35/1009* (2013.01); *B01J 35/1014* (2013.01); *B01J 37/26* (2013.01); *B01J 38/12* (2013.01); *C07C 17/206* (2013.01); *C07C 17/25* (2013.01); *Y02P 20/584* (2015.11)

(56) References Cited

FOREIGN PATENT DOCUMENTS

| | | |
|---|---|---|
| WO | 9810862 A1 | 3/1998 |
| WO | 2005037431 A1 | 4/2005 |
| WO | 2007019353 A1 | 2/2007 |

OTHER PUBLICATIONS

Written Opinion (PCT/ISA/237) dated Nov. 15, 2017, by the European Patent Office as the International Searching Authority for International Application No. PCT/FR2017/052286.

Adamczyk, B, et al., "Fluorine modified chromium oxide and its impact on heterogeneously catalyzed fluorination reactions", Journal of Fluorine Chemistry, Feb. 1, 2000, pp. 239-246, vol. 101, No. 2.

Bonniface, David W., et al., "Halogen exchange reactions for CFC alternatives. The behaviour of fluorine-18 labelled hydrogen fluoride towards prefluorinated chromia containing nickel(II) or zinc(II)", Green Chemistry, Feb. 1, 1999, pp. 9-11, retrieved from the internet: http://pubs.rsc.org/en/content/articlepdf/1999/gc/a808021f.

Mao, Wei, et al., "Catalytic gas-phase fluorination of 1,1,2,3-tetrachloropropene to 2-chloro-3,3,3-trifluoropropene over the fluorinated $Cr_2O_3$-based catalysts", Applied Catalysis A: General, Feb. 1, 2015, pp. 37-44, vol. 491.

Teinz, Katharina, et al., "Catalytic formation of 2,3,3,3-tetrafluoropropene from 2-chloro-3,3,3-trifluoropropene at fluorinated chromia: A study of reaction pathways", Applied Catalysis B: Environmental, Apr. 1, 2015, pp. 200-208, vol. 165.

Zhu, Y, et al., "Aliovalent-substituted chromium-based catalysts for the hydrofluorination of tetrachloroethylene", Journal of Catalysis, Oct. 1, 2001, pp. 8-16, vol. 291, No. 1.

* cited by examiner

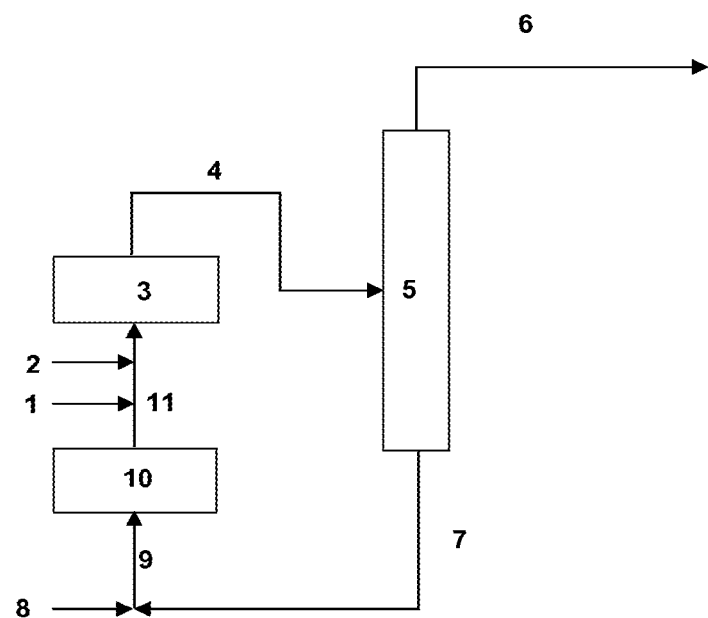

COMPOSITIONS OF CHROMIUM OXYFLUORIDE OR FLUORIDE CATALYSTS, THEIR PREPARATION AND THEIR USE IN GAS-PHASE PROCESSES

TECHNICAL FIELD

The present invention relates to catalytic chromium oxyfluoride or fluoride catalysts and to their use in a gas-phase process. The present invention also relates to the preparation of the said catalytic chromium oxyfluoride or fluoride compositions.

CONTEXT OF THE INVENTION

Halogenated hydrocarbons, in particular fluorinated hydrocarbons, such as hydrofluoroolefins, are compounds which have a structure of use as functional materials, solvents, refrigerants, blowing agents and monomers for functional polymers or starting materials for such monomers. Hydrofluoroolefins, such as 2,3,3,3-tetrafluoropropene (HFO-1234yf), are attracting attention because they offer a promising behaviour as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes can be carried out in the gas phase or in the liquid phase, in the absence or not of a catalyst.

The gas-phase processes are usually carried out in the presence of catalysts, in particular in the presence of chromium-based catalysts. US 2015/0148571 discloses a process for the production of fluorine-containing olefin where the catalyst is highly crystalline chromium oxide. WO 2005/037431 discloses a chromium-containing catalytic composition comprising $ZnCr_2O_4$ and a crystalline α-chromium oxide and its use in a process for modifying the distribution of fluorine in a halogenated hydrocarbon or for incorporating fluorine in a saturated or unsaturated hydrocarbon. WO 2007/019353 discloses the manufacture of 1,1,1,3,3-pentafluoropropane and 1,1,1,2,3-pentafluoropropane from a halopropene of formula $CX_3CCl=CCIX$ in the presence of a crystalline α-chromium oxide, where at least 0.05% of the chromium atoms in the lattice of the α-chromium oxide are replaced with a divalent copper. WO 98/10862 reveals a fluorination catalyst based on chromium(III) oxide, in which the chromium(III) oxide is at least partially and can contain a zinc atom or one of its compounds. The catalyst was used in a process for the manufacture of HFC-134a. A fluoro-chromium oxide having a fluorine content of at least 30% by weight is also used as catalyst in a process for the production of fluorine-containing olefins as disclosed in EP 2 223 906.

There also exists a need for catalytic compositions having a high activity (conversion) and/or selectivity and also for industrial chemical processes over the lifetime of a catalyst.

SUMMARY OF THE INVENTION

In a first aspect, the present invention relates to a process for modifying the fluorine distribution of a hydrocarbon compound in the presence of a catalyst, where the catalyst is a solid composition containing at least one component containing a chromium oxyfluoride or fluoride of empirical formula $Cr_xM_{(1-x)}O_rF_s$, where 2r+s is greater than or equal to 2.9 and less than 6, M is a metal chosen from a column between 2 and 12 of the Periodic Table of the Elements, x lies between 0.9 and 1, s is greater than 0 and less than or equal to 6 and r is greater than or equal to 0 and less than 3, the said solid composition having a crystallinity of less than 20% by weight.

In a preferred embodiment, the said solid composition has a crystallinity of less than 15%, preferably of less than 10%, more preferably of less than 5%, ideally of less than 1%, by weight; in particular, the said component containing chromium oxyfluoride or fluoride is amorphous.

In a preferred implementation, the said component containing chromium oxyfluoride or fluoride is of empirical formula $Cr_xM_{(1-x)}O_rF_s$, where M is chosen from the group consisting of Zn, Mg, Co, Mn and Ni, preferably Zn; in particular, x has a value between 0.9 and 1, preferably between 0.9 and 0.999, more preferably from 0.94 to 0.99.

In a preferred implementation, the solid composition contains at least one component containing chromium oxyfluoride or fluoride of empirical formula $CrO_rF_s$, where 2r+s is greater than or equal to 3 and less than 6, s is greater than 0 and less than or equal to 6 and r is greater than or equal to 0 and less than 3.

In a preferred implementation, the said hydrocarbon compound is of formula (I) $CX(Y)_2-CX(Y)_m-CH_mXY$, where X and Y independently represent H, F or Cl and m=0 or 1 with at least one from X or Y being Cl or F.

In a preferred implementation, the said hydrocarbon compound is chosen from the group consisting of tetrachloropropene, chlorotrifluoropropene, pentachloropropane, dichlorotrifluoropropane, trichlorodifluoropropane, tetrachlorofluoropropane, dichlorodifluoropropene, trichlorofluoropropene, tetrafluorochloropropane, pentafluoropropane and their mixtures; preferably, the hydrocarbon compound is chosen from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za), 1,3,3,3-tetrachloro-1-propene (HCO-1230zd), 1,1,1,2,2-pentafluoropropane (HFC-245cb) and 1-chloro-3,3,3-trifluoro-1-propene (HCFO-1233zd).

In a preferred implementation, the fluorine content of the hydrocarbon compound is increased by reacting the said compound with hydrogen fluoride in the gas phase in the presence of the said solid composition, the hydrocarbon compound being a saturated halogenated hydrocarbon or an unsaturated halogenated hydrocarbon or an unsaturated hydrocarbon.

In a preferred implementation, the fluorine content of the hydrocarbon compound is reduced by dehydrofluorination, the said hydrocarbon compound being in the presence of the said solid composition, the said hydrocarbon compound being a fluorinated hydrocarbon compound.

Otherwise, the chlorine content of the hydrocarbon compound is reduced by dehydrochlorination, the said hydrocarbon compound being in the presence of the said solid composition, the said hydrocarbon compound being a chlorinated hydrocarbon compound.

In a preferred implementation, the fluorine distribution in the hydrocarbon compound is modified by isomerizing the said hydrocarbon compound in the presence of the said solid composition, the said hydrocarbon compound being a fluorinated hydrocarbon compound.

In a preferred implementation, the fluorine distribution in the hydrocarbon compound is modified by disproportionating the said hydrocarbon compound in the gas phase in the presence of the said solid composition, the said hydrocarbon compound being a chlorofluorinated hydrocarbon compound.

In a preferred implementation, the fluorine content of the hydrocarbon compound is decreased by reacting the said hydrocarbon compound with hydrogen chloride in the gas phase in the presence of the said solid composition, the said hydrocarbon compound being a halogenated hydrocarbon compound comprising at least one fluorine atom.

In a preferred implementation, the fluorine content of a first hydrocarbon compound is increased by reacting the said first hydrocarbon compound with hydrogen fluoride in the gas phase in the presence of a solid composition, the first hydrocarbon compound being a saturated halogenated hydrocarbon or an unsaturated halogenated hydrocarbon or an unsaturated hydrocarbon, and the fluorine content of a second hydrocarbon compound is reduced by dehydrofluorination of the said second hydrocarbon compound in the presence of the said solid composition, the said second hydrocarbon compound being a fluorinated hydrocarbon compound.

In a preferred implementation, the fluorine content of a first hydrocarbon compound is increased by reacting the said hydrocarbon compound with hydrogen fluoride in the gas phase in the presence of a solid composition, the first hydrocarbon compound being a saturated halogenated hydrocarbon or an unsaturated halogenated hydrocarbon or an unsaturated hydrocarbon, and the chlorine content of a second hydrocarbon compound is reduced by dehydrochlorinating the said second hydrocarbon compound in the presence of the said solid composition, the said second hydrocarbon compound being a fluorinated hydrocarbon compound.

In a preferred implementation, the component containing chromium oxyfluoride or fluoride is of empirical formula $Cr_xM_{(1-x)}O_rF_s$, where r is greater than or equal to 0 and less than 2.62, s is greater than or equal to $[(0.16\ r)+0.52)]/0.92$, provided that s is greater than or equal to 0.76 and less than 6.

In a preferred implementation, the component containing chromium oxyfluoride or fluoride is of empirical formula $CrO_rF_s$, where r is greater than or equal to 0 and less than 2.62 and s is greater than or equal to $[(0.16\ r)+0.52)]/0.92$, provided that s is greater than or equal to 0.76 and less than 6.

In a preferred implementation, the component containing chromium fluoride is $CrF_3$, preferably an amorphous $CrF_3$, more preferably an anhydrous amorphous $CrF_3$.

In a preferred implementation, the solid composition comprises a support chosen from the group consisting of activated carbon, alumina, magnesium fluoride and aluminium fluoride.

In a preferred implementation, the solid composition has a specific surface between 1 and 100 $m^2/g$, preferably between 5 and 80 $m^2/g$, more preferably between 5 and 70 $m^2/g$, more preferably between 5 and 50 $m^2/g$, in particular between 10 and 50 $m^2/g$, very particularly between 15 and 45 $m^2/g$. Preferably, the solid composition has a specific surface between 1 and 80 $m^2/g$.

In a preferred implementation, the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3)]/0.8$, provided that s is greater than or equal to 1.90 and less than 6, preferably of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6, and with a specific surface between 10 and 50 $m^2/g$.

In a preferred implementation, the component containing chromium oxyfluoride or fluoride is of empirical formula $CrO_rF_s$, where r is greater than or equal to 0 and less than 2.05, s is greater than or equal to $[(0.4\ r)+1.3)]/0.8$, provided that s is greater than or equal to 1.90 and less than 6, preferably of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6, and with a specific surface between 10 and 50 $m^2/g$.

In a second aspect of the present invention, there is produced a solid composition, the said solid composition comprising a component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid catalytic composition having a crystallinity of less than 20% by weight.

In a preferred embodiment, the said solid composition has a crystallinity of less than 15%, preferably of less than 10%, more preferably of less than 5%, ideally of less than 1%, by weight; in particular, the said solid composition is amorphous.

In a preferred implementation, the said component containing chromium oxyfluoride or fluoride is of empirical formula $Cr_xM_{(1-x)}O_rF_s$, where M is chosen from the group consisting of Zn, Mg, Co, Mn and Ni, preferably Zn; in particular, x has a value between 0.9 and 1, preferably between 0.9 and 0.999, more preferably between 0.94 and 0.99.

In particular, the component containing chromium oxyfluoride or fluoride is of empirical formula $Cr_xM_{(1-x)}O_rF_s$, where M is chosen from the group consisting of Zn, Mg, Co, Mn and Ni, preferably Zn; in particular, x has a value between 0.9 and 1, preferably between 0.9 and 0.999, more preferably between 0.94 and 0.99.

In another implementation, there is produced a solid composition comprising a component containing chromium oxyfluoride or fluoride of empirical formula $CrO_rF_s$, where 2r+s is greater than or equal to 3.0 and less than 6, s is greater than 0 and less than or equal to 6 and r is greater than or equal to 0 and less than 3, the said catalytic composition having a crystallinity of less than 20% by weight. In a preferred implementation, the chromium-containing component is a component containing chromium fluoride, preferably $CrF_3$, more preferably amorphous $CrF_3$, ideally anhydrous amorphous $CrF_3$.

BRIEF DESCRIPTION OF THE ILLUSTRATIONS

The Figure represents a diagrammatic view of a process according to one implementation of the present invention.

DETAILED DESCRIPTION OF THE INVENTION

In a first aspect of the present invention, a process for modifying the fluorine distribution in a hydrocarbon compound in the presence of a catalyst is provided. In this process, a solid composition comprising at least one component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20% by weight, is used as catalyst.

The catalysts provided according to the present invention can be used to modify the fluorine distribution in hydrocarbon compounds, the latter being halogenated or non-halogenated hydrocarbon compounds. The fluorine distribution in a hydrocarbon compound can be modified by increasing the fluorine content of the hydrocarbon compound. The fluorine distribution of a hydrocarbon compound can also be modified by decreasing the fluorine content of the hydrocarbon compound and/or by rearranging the positions of fluorine atoms on the carbon atoms of the hydrocarbon compound.

The present invention can provide processes where the fluorine distribution in hydrocarbon compounds containing between one and twelve carbon atoms is modified, preferably processes where the fluorine distribution in hydrocarbon compounds containing between one and six common atoms is modified, in particular processes where the fluorine distribution in hydrocarbon compounds containing three carbon atoms is modified, more particularly where the fluorine distribution in halogenated hydrocarbon compounds containing three carbon atoms is modified. The present invention can provide processes where the fluorine content of hydrocarbon compounds containing between one and twelve carbon atoms is increased, preferably processes where the fluorine content of hydrocarbon compounds containing between one and six common atoms is increased, in particular processes where the fluorine content of hydrocarbon compounds containing three carbon atoms is increased, more particularly processes where the fluorine content of halogenated hydrocarbon compounds containing three carbon atoms is increased. The processes for modifying the fluorine distribution of hydrocarbon compounds, preferably of halogenated hydrocarbon compounds, include fluorination, chlorofluorination, isomerization, disproportionation, dehydrofluorination and chlorodefluorination.

The said solid composition can have a crystallinity of less than 15%, preferably of less than 10%, more preferably of less than 5%, ideally of less than 1%, by weight. In particular, the said component containing chromium oxyfluoride or fluoride can be amorphous. The term amorphous refers to a solid in which the atoms do not have an ordered atomic structure. Amorphous solids do not have internal structures which are repetitive at long range, as are found in crystals. The component containing chromium oxyfluoride or fluoride is amorphous when no signal representative of crystalline forms is detected by X-ray crystallography (crystalline diffraction figure).

The component containing chromium oxyfluoride or fluoride can be of empirical formula $Cr_xM_{(1-x)}O_rF_s$, where M is chosen from the group consisting of Zn, Mg, Co, Mn and Ni. The amount of zinc, nickel, cobalt, manganese or magnesium can lie between 0.1 mol % and 10 mol %, with respect to the solid composition, in particular between 1 mol % and 6 mol %, with respect to the solid composition. Preferably, M is zinc. More preferably, the solid composition contains zinc at a content of between 0.1 mol % and 10 mol %, with respect to the solid composition, in particular at a content of between 1 mol % and 6 mol %, with respect to the solid composition. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99.

In another implementation, the solid composition comprising a component containing chromium oxyfluoride or fluoride can be of empirical formula $CrO_rF_s$. In this case, no metal is present in the matrix of the component containing chromium oxyfluoride or fluoride. Then, in the empirical formula $Cr_xM_{(1-x)}O_rF_s$, x=1 and r and s are as defined in the present document, 2r+s being greater than or equal to 3.0 and less than 6.

The hydrocarbon compounds include those of general formula $C_hH_aBr_bCl_cF_d$, where h is an integer between 1 and 6, a is an integer between 0 and 13, b is an integer between 0 and 4, c is an integer between 0 and 13, d is an integer between 0 and 13, and the sum of a, b, c and d is equal to 2h+2; or those of general formula $C_pH_eBr_fCl_gF_h$, where p is an integer between 2 and 6, e is an integer between 0 and 10, f is an integer between 0 and 2, g is an integer between 0 and 12, h is an integer between 0 and 11, and the sum of e, f, g and h is equal to 2p.

Preferably, the hydrocarbon compounds include those of general formula $C_hH_aCl_cF_d$, where h is an integer between 2 and 4, a is an integer between 0 and 9, c is an integer between 0 and 9, d is an integer between 0 and 9, and the sum of a, c and d is equal to 2h+2; or those of general formula $C_pH_eCl_gF_h$, where p is an integer between 2 and 4, e is an integer between 0 and 8, g is an integer between 0 and 8, h is an integer between 0 and 7, and the sum of e, g and h is equal to 2p.

In particular, the hydrocarbon compounds which are suitable for the processes according to the present invention are of formula (I) $CX(Y)_2—CX(Y)_m—CH_mXY$, where X and Y independently represent H, F or Cl and m=0 or 1 with at least one from X or Y being Cl or F. Preferably, the hydrocarbon compounds can be chosen from the group consisting of tetrachloropropene, chlorotrifluoropropene, pentachloropropane, dichlorotrifluoropropane, trichlorodifluoropropane, tetrachlorofluoropropane, dichlorodifluoropropene, trichlorofluoropropene, pentafluoropropane and their mixtures.

Preferably, the hydrocarbon compounds can be chosen from the group consisting of 2-chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za), 1,3,3,3-tetrachloro-1-propene (HCO-1230zd), 1,1,1,2,2-pentafluoropropane (HFC-245cb) and 1-chloro-3,3,3-trifluoro-1-propene (HCFO-1233zd).

Preferably, the component containing chromium oxyfluoride or fluoride can be of empirical formula $Cr_xM_{(1-x)}O_rF_s$, where r is greater than or equal to 0 and less than 2.62, s is greater than or equal to [(0.16 r)+0.52]/0.92, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to [(0.24 r)+0.78]/0.88, provided that s is greater than or equal to 1.14 and less than 6, more preferably the component containing chromium oxyfluoride or fluoride is of empirical formula $Cr_xM_{(1-x)}O_rF_s$, where r is greater than or equal to 0 and less than 2.24, s is greater than or equal to [(0.32 r)+1.04]/0.84, provided that s is greater than or equal to 1.52 and less than 6, more preferably still the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3]/0.8$, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to $[(0.56\ r)+1.82]/0.72$, provided that s is greater than or equal to 2.50 and less than 6. More particularly, the compound containing chromium oxyfluoride or fluoride is of empirical formula $Cr_xM_{(1-x)}O_rF_s$ as defined in the present document and is amorphous, and more preferably anhydrous and amorphous. The component containing chromium fluoride can be $Cr_xM_{(1-x)}F_3$, preferably an amorphous $Cr_xM_{(1-x)}F_3$, more preferably an anhydrous amorphous $Cr_xM_{(1-x)}F_3$.

Preferably, the component containing chromium oxyfluoride or fluoride can be of empirical formula $CrO_rF_s$, where r is greater than or equal to 0 and less than 2.62, s is greater than or equal to $[(0.16\ r)+0.52]/0.92$, provided that s is greater than or equal to 0.76 and less than 6, more preferably the component containing chromium oxyfluoride or fluoride is of empirical formula $CrO_rF_s$, where r is greater than or equal to 0 and less than 2.43, s is greater than or equal to $[(0.24\ r)+0.78]/0.88$, provided that s is greater than or equal to 1.14 and less than 6, more preferably the component containing chromium oxyfluoride or fluoride is of empirical formula $CrO_rF_s$, where r is greater than or equal to 0 and less than 2.24, s is greater than or equal to $[(0.32\ r)+1.04]/0.84$, provided that s is greater than or equal to 1.52 and less than 6, more preferably still the component containing chromium oxyfluoride or fluoride is of empirical formula $CrO_rF_s$, where r is greater than or equal to 0 and less than 2.05, s is greater than or equal to $[(0.4\ r)+1.3]/0.8$, provided that s is greater than or equal to 1.90 and less than 6, in particular the component containing chromium oxyfluoride or fluoride is of empirical formula $CrO_rF_s$, where r is greater than or equal to 0 and less than 1.75, s is greater than or equal to $[(0.56\ r)+1.82]/0.72$, provided that s is greater than or equal to 2.50 and less than 6. In particular, the component containing chromium fluoride is $CrF_3$, preferably an amorphous $CrF_3$, more preferably an anhydrous amorphous $CrF_3$.

The solid composition can comprise a support chosen from the group consisting of activated carbon, alumina, graphite, magnesium fluoride and aluminium fluoride. Preferably, the solid composition has a specific surface between 1 and 100 m²/g, preferably between 5 and 80 m²/g, more preferably between 5 and 70 m²/g, ideally between 5 and 50 m²/g, in particular between 10 and 50 m²/g, more particularly between 15 and 45 m²/g.

An even more preferential catalyst is a solid composition comprising a component containing chromium oxyfluoride or fluoride of empirical formula $Cr_xM_{(1-x)}O_rF_s$, where r is greater than or equal to 0 and less than 2.05, s is greater than or equal to $[(0.4\ r)+1.3]/0.8$, provided that s is greater than or equal to 1.90 and less than 6, preferably of empirical formula $Cr_xM_{(1-x)}O_rF_s$, where r is greater than or equal to 0 and less than 1.75, s is greater than or equal to $[(0.56\ r)+1.82]/0.72$, provided that s is greater than or equal to 2.50 and less than 6, and with a specific surface between 10 and 50 m²/g. In particular, the solid composition comprises a component containing chromium oxyfluoride or fluoride of empirical formula $Cr_xM_{(1-x)}F_3$ and having a specific surface between 10 and 50 m²/g. More particularly, the component containing chromium oxyfluoride or fluoride is amorphous. More particularly still, M is zinc.

An even more preferential catalyst is a solid composition comprising a component containing chromium oxyfluoride or fluoride of empirical formula $CrO_rF_s$, where r is greater than or equal to 0 and less than 2.05, s is greater than or equal to $[(0.4\ r)+1.3]/0.8$, provided that s is greater than or equal to 1.90 and less than 6, preferably of empirical formula $CrO_rF_s$, where r is greater than or equal to 0 and less than 1.75, s is greater than or equal to $[(0.56\ r)+1.82]/0.72$, provided that s is greater than or equal to 2.50 and less than 6, and with a specific surface between 10 and 50 m²/g. In particular, the solid composition comprises a component containing chromium oxyfluoride or fluoride of empirical formula $CrF_3$ and with a specific surface between 10 and 50 m²/g. More particularly, the component containing chromium oxyfluoride or fluoride is amorphous.

In a first implementation, the fluorine content of the hydrocarbon compound is increased by reacting the said compound with hydrogen fluoride in the presence of the said solid composition, the hydrocarbon compound being a saturated halogenated hydrocarbon or an unsaturated halogenated hydrocarbon or an unsaturated hydrocarbon.

Hydrocarbon compounds suitable as starting reactants for the fluorination process of this first implementation can be saturated or unsaturated halogenated hydrocarbon compounds. The saturated halogenated hydrocarbon compounds include those of general formula $C_hH_aBr_bCl_cF_d$, where h is an integer between 1 and 6, a is an integer between 0 and 13, b is an integer between 0 and 4, c is an integer between 0 and 13, d is an integer between 0 and 13, and the sum of a, b, c and d is equal to 2h+2, provided that b+c is at least equal to 1. Preferably, the saturated halogenated hydrocarbon compounds include those of general formula $C_hH_aCl_cF_d$, where h is an integer between 2 and 4, a is an integer between 0 and 9, c is an integer between 0 and 9, d is an integer between 0 and 9, and the sum of a, c and d is equal to 2h+2. The unsaturated halogenated hydrocarbon compounds include those of general formula $C_pH_eBr_fCl_gF_h$, where p is an integer between 2 and 6, e is an integer between 0 and 11, f is an integer between 0 and 2, g is an integer between 0 and 12, h is an integer between 0 and 11, the sum of f, g and h is at least 1 and the sum of e, f, g and h is equal to 2p. Preferably, the unsaturated halogenated hydrocarbon compounds include those of general formula $C_pH_eCl_gF_h$, where p is an integer between 2 and 4, e is an integer between 0 and 8, g is an integer between 0 and 8, h is an integer between 0 and 7, and the sum of e, g and h is equal to 2p. The fluorine content of the saturated halogenated hydrocarbon compounds of formula $C_hH_aBr_bCl_cF_d$ or of the unsaturated halogenated hydrocarbon compounds of formula $C_pH_eBr_fCl_gF_h$, as defined above, can be increased by reacting the said hydrocarbon compounds with HF in the vapour phase in the presence of a catalyst which is a solid composition comprising at least one component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20% by weight, advantageously of less than 15%, preferably of less than 10%, more preferably of less than 5%, ideally of less than 1%, by weight; in particular, the said solid composition is amorphous.

Preferably, the component containing chromium oxyfluoride or fluoride can be of empirical formula $Cr_xM_{(1-x)}O_rF_s$, where r is greater than or equal to 0 and less than 2.62, s is greater than or equal to $[(0.16\ r)+0.52]/0.92$, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to [(0.24 r)+0.78)]/0.88, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to [(0.32 r)+1.04)]/0.84, provided that s is greater than or equal to 1.52 and less than 6, more preferably still the component containing chromium oxyfluoride or fluoride is of empirical formula $Cr_xM_{(1-x)}O_rF_s$, where r is greater than or equal to 0 and less than 2.05, s is greater than or equal to [(0.4 r)+1.3)]/0.8, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to [(0.56 r)+1.82)]/0.72, provided that s is greater than or equal to 2.50 and less than 6. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above.

In particular, the said component containing chromium oxyfluoride or fluoride is a component containing chromium fluoride, preferably $CrF_3$, more preferably an amorphous $CrF_3$, ideally an anhydrous amorphous $CrF_3$.

In a preferred implementation, the solid composition comprises a support chosen from the group consisting of activated carbon, alumina and aluminium fluoride. Preferably, the solid composition has a specific surface between 1 and 100 m²/g, preferably between 5 and 80 m²/g, more preferably between 5 and 70 m²/g, ideally between 5 and 50 m²/g, in particular between 10 and 50 m²/g, more particularly between 15 and 45 m²/g.

In particular, the component containing chromium oxyfluoride or fluoride is of empirical formula $Cr_xM_{(1-x)}O_rF_s$, where r is greater than or equal to 0 and less than 2.05, s is greater than or equal to [(0.4 r)+1.3)]/0.8, provided that s is greater than or equal to 1.90 and less than 6, preferably of empirical formula $Cr_xM_{(1-x)}O_rF_s$, where r is greater than or equal to 0 and less than 1.75, s is greater than or equal to [(0.56 r)+1.82)]/0.72, provided that s is greater than or equal to 2.50 and less than 6, and with a specific surface between 10 and 50 m²/g. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above and with a specific surface between 10 and 50 m²/g.

The process according to the first implementation can be carried out in a reactor comprising a catalytic bed containing a catalyst and according to the following operating conditions:

- an HF/hydrocarbon compound molar ratio between 1:1 and 150:1, preferably between 2:1 and 125:1, more preferably between 3:1 and 100:1;
- a contact time between 1 and 100 s, preferably between 2 and 75 s, in particular between 3 and 50 s;
- a pressure between atmospheric pressure and 20 bar, preferably between 2 and 18 bar, more preferably between 3 and 15 bar;
- a temperature (of the catalytic bed) between 200 and 450° C., preferably between 250 and 400° C., more preferably between 280° C. and 380° C.

The process can be successfully carried out over a period of time of between 10 and 8000 h, preferably between 50 and 5000 h, more preferably between 70 and 1000 h.

An oxidant, such as oxygen or chlorine, can be added during the process. The molar ratio of the oxidant to the hydrocarbon compound can be between 0.005 and 2, preferably between 0.01 and 1.5. The oxidant can be pure oxygen, air or a mixture of oxygen and nitrogen.

The process is typically carried out in a tubular reactor. The reactor and its associated feed lines, effluent lines and associated devices have to be constructed from materials which are resistant to hydrogen fluoride and to hydrogen chloride. Typical construction materials, well known in the state of the art of fluorination, include stainless steels, in particular of austenitic type, well-known alloys having a high nickel content, such as Monel® nickel/copper alloys, Hastelloy® nickel-based alloys and Inconel® nickel/chromium alloys.

The amount of HF reacted with the hydrocarbon compounds has to be at least stoichiometric. The stoichiometric amount is based on the number of H, Br and/or Cl substituents to be replaced by F, in addition to one mole of HF in order to saturate the carbon-carbon double bond, if there is one of them.

Examples of saturated halogenated compounds of formula $C_nH_aBr_bCl_cF_d$ which can be reacted with HF in the presence of the catalysts of this invention include $CH_2Cl_2$, $CH_2Br_2$, $CHCl_3$, $CCl_4$, $C_2Cl_6$, $C_2BrCl_5$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_2HBrF_4$, $C_2H_2Cl_4$, $C_2H_2Cl_3F$, $C_2H_2Cl_2F_2$, $C_2H_2ClF_3$, $C_2H_3Cl_3$, $C_2H_3Cl_2F$, $C_2H_3ClF_2$, $C_2H_4Cl_2$, $C_2H_4ClF$, $C_3Cl_6F_2$, $C_3Cl_5F_3$, $C_3Cl_4F_4$, $C_3Cl_3F_5$, $C_3HCl_7$, $C_3HCl_6F$, $C_3HCl_5F_2$, $C_3HCl_4F_3$, $C_3HCl_3F_4$, $C_3HCl_2F_5$, $C_3Cl_2F_6$, $C_3H_2Cl_6$, $C_3H_2BrCl_5$, $C_3H_2Cl_5F$, $C_3H_2Cl_4F_2$, $C_3H_2Cl_3F_3$, $C_3H_2Cl_2F_4$, $C_3H_2ClF_5$, $C_3H_3Cl_5$, $C_3H_3Cl_4F$, $C_3H_3Cl_3F_2$, $C_3H_3Cl_2F_3$, $C_3H_3ClF_4$, $C_3H_4Cl_4$, $C_4Cl_4Cl_4$, $C_4Cl_4Cl_6$, $C_4H_6Cl_6$, $C_4H_5Cl_4F_1$ and $C_6H_4Cl_8$.

Specific examples of reactions for the fluorination of saturated halogenated hydrocarbon compounds which can be successfully carried out under the conditions described above by using the catalysts of this invention include the conversion of 1,1,2-trichloroethane ($CHCl_2CH_2Cl$ or HCC-140) into 1-chloro-2,2-difluoroethane ($CH_2ClCF_2H$ or HCFC-142), the conversion of 1,1,1,3,3,3-hexachlorodifluoropropane ($CCl_3CF_2CCl_3$ or CFC-212ca) into a mixture of 1,1,3-trichloro-1,2,2,3,3-pentafluoropropane ($CCl_2FCF_2CClF_2$ or CFC-215ca) and 1,3-dichloro-1,1,2,2,3,3-hexafluoropropane ($CClF_2CF_2CClF_2$ or CFC-216ca), the conversion of 1,1,1,3,3,3-hexachloropropane ($CCl_3CH_2CCl_3$ or HCC-230fa) into 1-chloro-1,3,3,3-pentafluoropropane ($CF_3CH_2CClF_2$ or HCFC-235fa) and 1,1,1,3,3,3-hexafluoropropane ($CF_3CH_2CF_3$ or HFC-236fa), the conversion of 1,1,1,3,3-pentachloropropane ($CCl_3CH_2CHCl_2$ or HCC-240fa) into a mixture of 1,1,1,3,3-pentafluoropropane ($CHF_2CH_2CF_3$ or HFC-245fa), 1-chloro-3,3,3-trifluoro-1-propene ($CHCl=CHCF_3$ or HCFO-1233zd) and 1,3,3,3-tetrafluoropropene ($CHF=CHCF_3$ or HFO-1234ze), the conversion of 2,2,3-trichloro-1,1,1,3,3-pentafluoropropane ($CF_3CCl_2CClF_2$ or CFC-215aa) into a mixture of 1,1,1,3,3,3-hexachlorodifluoropropane ($CF_3CCl_2CF_3$ or CFC-212ca) and 2-chloro-1,1,1,2,3,3,3-heptafluoropropane ($CF_3CClFCF_3$ or CFC-217ba), the conversion of 1,1,1,3,3,3-hexachlorodifluoropropane ($CF_3CCl_2CF_3$ or CFC-212ca) into 2-chloro-1,1,1,2,3,3,3- heptafluoropropane ($CF_3ClFCF_3$ or CFC-217ba), the conversion of a mixture containing 1,1-dichloro-2,2,3,3,3-pentafluoropropane ($CF_3CF_2CHCl_2$ or HCFC-225ca) and 1,3-dichloro-1,2,2,3,3-pentafluoropropane ($CClF_2CF_2CHClF$ or HCFC-225cb) into a mixture of 1-chloro-1,2,2,3,3,3-hexafluoropropane ($CF_3CF_2CHClF$ or HCFC-226ca) and 1,1,1,2,2,3,3-heptafluoropropane ($CF_3CF_2CHF_2$ or HFC-227ca), the conversion of 1,1,1,2,3-pentachloropropane ($CCl_3CHClCH_2Cl$ or HCC-240db) into 2-chloro-3,3,3-trifluoro-1-propene ($CF_3CCl=CH_2$ or HCFO-1233xf), the conversion of 1,1,2,2,3-pentachloropropane ($CHCl_2CCl_2CH_2Cl$ or HCC-240aa) into 2-chloro-3,3,3-trifluoro-1-propene ($CF_3CCl=CH_2$ or HCFO-1233xf), the conversion of 1,1,1,2,3-pentachloropropane ($CCl_3CHClCH_2Cl$ or HCC-240db) into 2,3,3,3-tetrafluoropropene ($CF_3CF=CH_2$ or HFO-1234yf), the conversion of 1,1,2,2,3-pentachloropropane ($CHCl_2CCl_2CH_2Cl$ or HCC-240aa) into 2,3,3,3-tetrafluoropropene ($CF_3CF=CH_2$ or HFO-1234yf), the conversion of 1,1,1,3,3-pentachloropropane ($CCl_3CH_2CHCl_2$ or HCC-240fa) into 1,3,3,3-tetrafluoropropene ($CF_3CH=CHF$ or HFO-1234ze), in particular the conversion of 1,1,1,2,3-pentachloropropane ($CCl_3CHClCH_2Cl$ or HCC-240db) into 2-chloro-3,3,3-trifluoro-1-propene ($CF_3CCl=CH_2$ or HCFO-1233xf), the conversion of 1,1,2,2,3-pentachloropropane ($CHCl_2CCl_2CH_2Cl$ or HCC-240aa) into 2-chloro-3,3,3-trifluoro-1-propene ($CF_3CCl=CH_2$ or HCFO-1233xf), the conversion of 1,1,1,2,3-pentachloropropane ($CCl_3CHClCH_2Cl$ or HCC-240db) into 2,3,3,3-tetrafluoropropene ($CF_3CF=CH_2$ or HFO-1234yf), the conversion of 1,1,2,2,3-pentachloropropane ($CHCl_2CCl_2CH_2Cl$ or HCC-240aa) into 2,3,3,3-tetrafluoropropene ($CF_3CF=CH_2$ or HFO-1234yf), the conversion of 1,1,1,3,3-pentachloropropane ($CCl_3CH_2CHCl_2$ or HCC-240fa) into 1,3,3,3-tetrafluoropropene ($CF_3CH=CHF$ or HFO-1234ze), the conversion of 1,1,2-trichloroethane ($CHCl_2CH_2Cl$ or HCC-140) into 1-chloro-2,2-difluoroethane ($CH_2ClCF_2H$ or HCFC-142).

Examples of unsaturated halogenated compounds of formulae $C_pH_eBr_fCl_gF_h$ and $C_iH_i$ which can be reacted with HF in the presence of the catalysts of this invention include $C_2Cl_4$, $C_2BrCl_3$, $C_2Cl_3F$, $C_2Cl_2F_2$, $C_2ClF_3$, $C_2F_4$, $C_2HCl_3$, $C_2HBrCl_2$, $C_2HCl_2F$, $C_2HClF_2$, $C_2HF_3$, $C_2H_2Cl_2$, $C_2H_2ClF$, $C_2H_2F_2$, $C_2H_3Cl$, $C_2H_3F$, $C_2H_4$, $C_3H_6$, $C_3H_5Cl$, $C_3H_4Cl_2$, $C_3H_3Cl_3$, $C_3H_2Cl_4$, $C_3HCl_5$, $C_3H_2ClF_3$, $C_3F_3HCl_2$, $C_3F_2H_2Cl_2$, $C_3F_4H$, $ClC_3Cl_6$, $C_3Cl_5F$, $C_3Cl_4F_2$, $C_3Cl_3F_3$, $C_3Cl_2F_4$, $C_3ClF_5$, $C_3HF_5$, $C_3H_2F_4$, $C_3F_6$, $C_4Cl_8$, $C_4Cl_2F_6$, $C_4ClF_7$, $C_4H_2F_6$ and $C_4HClF_6$.

Specific examples of reactions for the fluorination of unsaturated halogenated hydrocarbon compounds which can be successfully carried out by using the catalysts of this invention include the conversion of 1,2-dichloroethylene ($CHCl=CClH$ or HCO-1130) into 1-chloro-2,2-difluoroethane ($CH_2ClCF_2H$ or HCFC-142)$_2$, the conversion of 1,1,2-trichloro-3,3,3-trifluoro-1-propene ($CCl_2=CClCF_3$ or CFC-1213xa) into a mixture of 2,3-dichloro-1,1,1,3,3-pentafluoropropane ($CF_3CHClCClF_2$ or HCFC-225da), of 2-chloro-1,1,1,3,3,3-hexafluoropropane ($CF_3CHClCF_3$ or HCFC-226da) and/or of 2-chloro-1,1,3,3,3-pentafluoro-1-propene ($CF_3CCl=CF_2$ or CFC-1215xc), the conversion of hexafluoropropene ($CF_3CF=CF_2$ or CFC-1216yc) into 1,1,1,2,3,3,3-heptafluoropropane ($CF_3CHFCF_3$ or HFC-227ea), the conversion of 1,1,3,3,3-pentafluoropropene ($CF_3CH=CF_2$ or HFO-1225zc) into 1,1,1,3,3,3-hexafluoropropane ($CF_3CH_2CF_3$ or HFC-236fa), the conversion of 1,3,3,3-tetrafluoropropene ($CF_3CH=CHF$ or HFO-1234ze) into 1,1,1,3,3-pentafluoropropane ($CF_3CH_2CHF_2$ or HFC-245fa), the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf), the conversion of 1,1,2,3-tetrachloro-1-propene ($CCl_2=CClCH_2Cl$ or HCO-1230xa) into 2-chloro-3,3,3-trifluoro-1-propene ($CF_3CCl=CH_2$ or HCFO-1233xf) or 2,3,3,3-tetrafluoropropene ($CF_3CF=CH_2$ or HFO-1234yf), the conversion of 2,3,3,3-tetrachloro-1-propene ($CCl_3CCl=CH_2$ or HCO-1230xf) into 2-chloro-3,3,3-trifluoro-1-propene ($CF_3CCl=CH_2$ or HCFO-1233xf) or into 2,3,3,3-tetrafluoropropene ($CF_3CF=CH_2$ or HFO-1234yf), the conversion of 1-chloro-3,3,3-trifluoro-1-propene ($CF_3CH=CHCl$ or HCFO-1233zd) or 1,1,3,3-tetrachloro-1-propene ($CCl_2=CHCHCl_2$ or HCO-1230za) or 1,3,3,3-tetrachloroprop-1-ene ($CCl_3CH=CHCl$ or HCO-1230zd) into 1,3,3,3-tetrafluoropropene ($CF_3CH=CHF$ or HFO-1234ze), in particular the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf), the conversion of 1,1,2,3-tetrachloro-1-propene ($CCl_2=CClCH_2Cl$ or HCO-1230xa) into 2-chloro-3,3,3-trifluoro-1-propene ($CF_3CCl=CH_2$ or HCFO-1233xf) or into 2,3,3,3-tetrafluoropropene ($CF_3CF=CH_2$ or HFO-1234yf), the conversion of 2,3,3,3-tetrachloro-1-propene ($CCl_3Cl=CH_2$ or HCO-1230xf) into 2-chloro-3,3,3-trifluoro-1-propene ($CF_3CCl=CH_2$ or HCFO-1233xf) or into 2,3,3,3-tetrafluoropropene ($CF_3CF=CH_2$ or HFO-1234yf), the conversion of 1-chloro-3,3,3-trifluoro-1-propene ($CF_3CH=CHCl$ or HCFO-1233zd) or of 1,1,3,3-tetrachloro-1-propene ($CCl_2=CHCHCl_2$ or HCO-1230za) or of 1,3,3,3-tetrachloroprop-1-ene ($CCl_3CH=CHCl$ or HCO-1230zd) into 1,3,3,3-tetrafluoropropene ($CF_3CH=CHF$ or HFO-1234ze), the conversion of 1,2-dichloroethylene ($CHCl=CClH$ or HCO-1130) into 1-chloro-2,2-difluoroethane ($CH_2ClCF_2H$ or HCFC-142).

Preferably, the hydrocarbon compound is chosen from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 1,1,2,3-tetrachloro-1-propene (HCO-1230xa), 2,3,3,3-tetrachloro-1-propene (HCO-1230xf), or their mixtures, for the production of 2,3,3,3-tetrafluoropropene (HFO-1234yf).

Otherwise, the hydrocarbon compound is chosen from the group consisting of 1-chloro-3,3,3-trifluoro-1-propene (HCFO-1233zd), 1,1,1,3,3-pentachloropropane (HCC-240fa), 1,1,3,3-tetrachloro-1-propene (HCO-1230za), 1,3,3,3-tetrachloro-1-propene (HCO-1230zd), or their mixtures, for the production of 1,3,3,3-tetrafluoropropene (HFO-1234ze).

In a second implementation, the fluorine content of the hydrocarbon compound is reduced by dehydrofluorinating the said hydrocarbon compound in the presence of the said solid composition, the said hydrocarbon compound being a fluorinated hydrocarbon compound.

The fluorinated hydrocarbon compounds suitable as starting materials in the dehydrofluorination process of this invention are typically saturated. The saturated halogenated hydrocarbon compounds include those of general formula $C_nH_aF_d$, where n is an integer between 2 and 6, a is an integer between 1 and 13, d is an integer between 1 and 13, and the sum of a and d is equal to 2n+2. The fluorine content of the saturated compounds of formula $C_nH_aF_d$ can be reduced in the presence of a catalyst which is a solid composition comprising at least one component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20% by weight, advantageously of less than 15%, preferably of less than 10%, more preferably of less than 5%, ideally of less than 1%, by weight; in particular, the said solid composition is amorphous. In particular, M is zinc.

Preferably, the component containing chromium oxyfluoride or fluoride can be of empirical formula $Cr_xM_{(1-x)}O_rF_s$, where r is greater than or equal to 0 and less than 2.62, s is greater than or equal to $[(0.16\ r)+0.52)]/0.92$, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to $[(0.24\ r)+0.78)]/0.88$, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to $[(0.32\ r)+1.04)]/0.84$, provided that s is greater than or equal to 1.52 and less than 6, more ideally still the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3)]/0.8$, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above.

In particular, the said component containing chromium oxyfluoride or fluoride is a component containing chromium fluoride, preferably $CrF_3$, more preferably an amorphous $CrF_3$, ideally an anhydrous amorphous $CrF_3$.

In a preferred implementation, the solid composition contains a support chosen from the group consisting of activated carbon, alumina and aluminium fluoride. Preferably, the solid composition has a specific surface between 1 and 100 m$^2$/g, preferably between 5 and 80 m$^2$/g, preferably between 5 and 70 m$^2$/g, ideally between 5 and 50 m$^2$/g, in particular between 10 and 50 m$^2$/g, more particularly between 15 and 45 m$^2$/g.

In particular, the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3)]/0.8$, provided that s is greater than or equal to 1.90 and less than 6, preferably of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6, and with a specific surface between 10 and 50 m$^2$/g. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above and a specific surface between 10 and 50 m$^2$/g.

The process according to the second implementation can be carried out in a reactor comprising a catalytic bed containing a catalyst and according to the following operating conditions:
- an HF/hydrocarbon compound molar ratio between 1:1 and 150:1, preferably between 2:1 and 125:1, more preferably between 3:1 and 100:1;
- a contact time between 1 and 100 s, preferably between 2 and 75 s, in particular between 3 and 50 s;
- a pressure between atmospheric pressure and 20 bar, preferably between 2 and 18 bar, more preferably between 3 and 15 bar;
- a temperature (of the catalytic bed) between 200 and 450° C., preferably between 250 and 400° C., more preferably between 280° C. and 380° C.

The process can be successfully carried out over a period of time of between 10 and 8000 h, preferably between 50 and 5000 h, more preferably between 70 and 1000 h.

An oxidant, such as oxygen or chlorine, can be added during the process. The molar ratio of the oxidant to the hydrocarbon compound can be between 0.005 and 2, preferably between 0.01 and 1.5. The oxidant can be pure oxygen, air or a mixture of oxygen and nitrogen.

The process is typically carried out in a tubular reactor. The reactor and its associated feed lines, effluent lines and associated devices have to be constructed from materials which are resistant to hydrogen chloride. Typical construction materials, well known in the state of the art of fluorination, include stainless steels, in particular of austenitic type, well-known alloys having a high nickel content, such as Monel® nickel/copper alloys, Hastelloy® nickel-based alloys and Inconel® nickel/chromium alloys.

The product of the dehydrofluorination reaction consists of HF and of the unsaturated fluorinated hydrocarbon compound resulting from the loss of HF by the initial reactant. Specific examples of gas-phase dehydrofluorination reactions which can be carried out by using the catalysts of this invention include the conversion of 1,1-difluoroethane ($CHF_2CH_3$ or HFC-152a) into vinyl fluoride ($CHF=CH_2$ or HFO-1141), the conversion of 1,1,1-trifluoroethane ($CF_3CH_3$ or HFC-143a) into vinylidene fluoride ($CF_2=CH_2$ or HFO-1132a), the conversion of 2-chloro-1,1,1-trifluoroethane ($CF_3CH_2Cl$ or HCFC-133a) into 2-chloro-1,1-difluoroethylene ($CF_2=CHCl$ or HCFO-1122), the conversion of 1,1,1,2-tetrafluoroethane ($CF_3CH_2F$ or HFC-134a) into trifluoroethylene ($CF_2=CHF$ or HFO-1123), the conversion of 1,1,2,2-tetrafluoroethane ($CHF_2CHF_2$ or HFC-134) into trifluoroethylene ($CF_2=CHF$ or HFO-1123), the conversion of 1,1,1,2-tetrafluoropropane ($CH_3CHFCF_3$ or HFC-254eb) into 1,1,1-trifluoropropene ($CH_2=CHCF_3$ or HFO-1243zf), the conversion of 1,1,1,3,3-pentafluoropropane ($CHF_2CH_2CF_3$ or HFC-245fa) into 1,3,3,3-tetrafluoropropene ($CHF=CHCF_3$ or HFO-1234ze), the conversion of 1,1,1,2,3,3-hexafluoropropane ($CHF_2CHFCF_3$ or HFC-236ea) into 1,2,3,3,3-pentafluoropropene ($CHF=CFCF_3$ or HFO-1225ye), the conversion of 1,1,1,3,3,3-hexafluoropropane ($CF_3CH_2CF_3$ or HFC-236fa) into 1,3,3,3-pentafluoropropene ($CF_3CH=CF_2$ or HFO-1225zc), the conversion of 1,1,1,2,3,3-hexafluoropropane ($CF_3CF_2CFH_2$ or HFC-236cb) into 1,2,3,3,3-pentafluoropropene ($CHF=CFCF_3$ or HFO-1225ye), the conversion of 1,1,1,2,2-pentafluoropropane ($CF_3CF_2CH_3$ or HFC-245cb) into 2,3,3,3-tetrafluoropropene ($CF_3CF=CH_2$ or HFO-1234yf) and the conversion of 1,1,1,2,3-pentafluoropropane ($CF_3CHFCH_2F$ or HFC-245eb) into 2,3,3,3-tetrafluoropropene ($CF_3CF=CH_2$ or HFO-1234yf).

In particular, the halogenated hydrocarbon compound is 1,1,1,2,2-pentafluoropropane (HFC-245cb) for the production of 2,3,3,3-tetrafluoropropene (HFO-1234yf). Otherwise, the halogenated hydrocarbon compound is 1,1,1,3,3-pentafluoropropane (HFC-245fa) for the production of 1,3,3,3-tetrafluoropropene (HFO-1234ze).

In the processes according to the first implementation and the second implementation, the reaction of the said hydrocarbon compound with hydrogen fluoride can be carried out in the presence of oxygen or of chlorine.

In a third implementation, the fluorine distribution in the hydrocarbon compound is modified by isomerizing the said hydrocarbon compound in the presence of the said solid composition, the said hydrocarbon compound being a fluorinated hydrocarbon compound.

In a fourth implementation, the fluorine distribution in the hydrocarbon compound is modified by disproportionating the said hydrocarbon compound in the gas phase in the presence of the said solid composition, the said hydrocarbon compound being a chlorofluorinated hydrocarbon compound.

The isomerization and disproportionation processes of the third and fourth implementations are successfully carried out in the vapour phase in the presence of a catalyst which is a solid composition comprising at least one component containing chromium oxyfluoride or fluoride of empirical formula $Cr_xM_{(1-x)}O_rF_s$, where $2r+s$ is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20%, advantageously of less than 15%, preferably of less than 10%, more preferably of less than 5%, ideally of less than 1%, by weight; in particular, the said solid composition is amorphous. In particular, M is zinc.

Preferably, the component containing chromium oxyfluoride or fluoride can be of empirical formula $Cr_xM_{(1-x)}O_rF_s$, where r is greater than or equal to 0 and less than 2.62, s is greater than or equal to $[(0.16\ r)+0.52)]/0.92$, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to $[(0.24\ r)+0.78)]/0.88$, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to $[(0.32\ r)+1.04)]/0.84$, provided that s is greater than or equal to 1.52 and less than 6, more ideally still the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3)]/0.8$, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above.

In particular, the said component containing chromium oxyfluoride or fluoride is a component containing chromium fluoride, preferably $CrF_3$, more preferably an amorphous $CrF_3$, ideally an anhydrous amorphous $CrF_3$.

In a preferred implementation, the solid composition comprises a support chosen from the group consisting of activated carbon, alumina and aluminium fluoride. Preferably, the solid composition has a specific surface between 1 and 100 m$^2$/g, preferably between 5 and 80 m$^2$/g, more preferably between 5 and 70 m$^2$/g, ideally between 5 and 50 m$^2$/g, in particular from 10 to 50 m$^2$/g, more particularly from 15 to 45 m$^2$/g.

In particular, the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3)]/0.8$, provided that s is greater than or equal to 1.90 and less than 6, preferably of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6, and with a specific surface between 10 and 50 m$^2$/g. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above and with a specific surface between 10 and 50 m$^2$/g.

The fluorinated hydrocarbon compounds appropriate as starting materials for the isomerization and disproportionation processes can be saturated or unsaturated. The saturated fluorinated hydrocarbon compounds appropriate for the isomerization and disproportionation processes include those of general formula $C_nH_aBr_bCl_cF_d$, where n is an integer between 2 and 6, a is an integer between 0 and 13, b is an integer between 0 and 4, c is an integer between 0 and 13, d is an integer between 1 and 13, and the sum of a, b, c and d is equal to $2n+2$, provided that $a+b+c \geq 1$. The unsaturated fluorinated hydrocarbon compounds appropriate for the isomerization and disproportionation processes include those of general formula $C_pH_eBr_fCl_gF_h$, where p is an integer between 2 and 6, e is an integer between 0 and 11, f is an integer between 0 and 2, g is an integer between 0 and 12, h is an integer between 1 and 11, and the sum of e, f, g and h is equal to $2p$, provided that the sum $e+f+g \geq 1$.

The fluorine distribution of a fluorinated hydrocarbon compound is modified by rearranging the H, Br, Cl and F substituents in the molecule (typically a thermodynamically preferential arrangement) while keeping the same number of H, Br, Cl and F substituents, respectively. In the present document, this process is known as isomerization.

The fluorine distribution of a fluorinated hydrocarbon compound is modified by exchanging at least one F substituent of the halogenated hydrocarbon starting material with at least one H, Br and/or Cl substituent of another molecule of the halogenated hydrocarbon starting material, so as to give the formation of one or more halogenated hydrocarbon compounds having a reduced fluorine content, with respect to the halogenated hydrocarbon starting material, and one or more halogenated hydrocarbon compounds having an increased fluorine content, with respect to the halogenated hydrocarbon starting material. In the present document, this process is known as disproportionation.

The isomerization and disproportionation reactions can take place simultaneously.

Whether an isomerization, a disproportionation or both an isomerization and a disproportionation are carried out, it is possible to modify the fluorine distribution of saturated compounds of formula $C_nH_aBr_bCl_cF_d$ and/or of unsaturated compounds of formula $C_pH_eBr_fCl_gF_h$ in the presence of a catalyst as disclosed above.

The isomerization and disproportionation processes are typically successfully carried out at temperatures between approximately 100° C. and 500° C., preferably between approximately 150° C. and approximately 400° C. The contacting time in the reactor is typically from approximately 1 to approximately 120 s, preferably from approximately 5 to approximately 60 s. The isomerization and disproportionation reactions can be successfully carried out in the presence of an inert gas, such as helium, argon or nitrogen, although this is not preferred. The isomerization and disproportionation reactions can be successfully carried out in the presence of HF and HCl.

Preferably, the isomerization processes can be carried out by using the present catalyst and include the conversion of 1-chloro-1,1-difluoroethane ($CH_3CF_2Cl$ or HCFC-142b) into 1-chloro-2,2-difluoroethane ($CH_2ClCF_2H$ or HCFC-142), the conversion of 1,3-dichloro-1,2,2,3,3-pentafluoropropane ($CHClFCF_2CF_2Cl$ or HCFC-225cb) into 1,1-dichloro-2,2,3,3,3-pentafluoropropane ($CHCl_2CF_2CF_3$ or HCFC-225ca), the conversion of 2,2-dichloro-1,1,1,3,3-pentafluoropropane ($CHF_2CCl_2CF_3$ or HCFC-225aa) into 1,1-dichloro-2,2,3,3,3-pentafluoropropane ($CHCl_2CF_2CF_3$ or HCFC-225ca), the conversion of 1,1,1,2,3-pentafluoropropane ($CF_3CHFCH_2F$ or HFC-245eb) into 1,1,1,2,2-pentafluoropropane ($CF_3CF_2CH_3$ or HFC-245cb), the conversion of 1,1,1,3,3,pentafluoropropane ($CHF_2CH_2CF_3$ or HFC-245fa) into 1,1,1,2,3-pentafluoropropane ($CF_3CHFCH_2F$ or HFC-245eb), the conversion of 1,3,3,3-tetrafluoropropene ($CHF=CHCF_3$ or HFO-1234ze) into 2,3,3,3-tetrafluoropropene ($CF_3CF=CH_2$ or HFO-1234yf), the conversion of 1,1,3,3-tetrafluoropropene ($CF_2=CHCHF_2$ or HFO-1234zc) into 1,3,3,3-tetrafluoropropene ($CHF=CHCF_3$ or HFO-1234ze), the conversion of 1-chloro-3,3,3-trifluoro-1-propene ($CHCl=CHCF_3$ or HCFO-1233zd) into 2-chloro-3,3,3-trifluoro-1-propene ($CH_2=CClCF_3$ or HCFO-1233xf) and the conversion of the (Z) isomer of hydrochlorofluoroolefins into the (E) isomer of hydrochlorofluoroolefins.

In particular, the (Z) isomers of hydrochlorofluoroolefins are the (Z) isomers of hydrochlorofluoropropenes and hydrochlorofluorobutenes. Specific examples include the conversion of (Z)-1-chloro-3,3,3-trifluoro-1-propene ($CHCl=CHCF_3$ or HCFO-1233zd(Z)) into (E)-1-chloro-3,3,3-trifluoro-1-propene ($CHCl=CHCF_3$ or HCFO-1233zd (E)), the conversion of (Z)-1,3,3,3-tetrafluoropropene ($CHF=CHCF_3$ or HFO-1234ze(Z)) into (E)-1,3,3,3-tetrafluoropropene ($CHF=CHCF_3$ or HFO-1234ze(E)), the conversion of (Z)-1,2,3,3,3-pentafluoropropene ($CHF=CFCF_3$ or HFO-1225ye(Z)) into (E)-1,2,3,3,3-pentafluoropropene ($CHF=CFCF_3$ or HFO-1225ye(E)) and the conversion of (Z)-1,1,1,4,4,4-hexafluoro-2-butene ($CF_3CH=CHCF_3$ or HFO-1336mzz(Z)) into (E)-1,1,1,4,4,4-hexafluoro-2-butene ($CF_3CH=CHCF_3$ or HFO-1336mzz (E)).

Preferably, the disproportionation processes can be carried out by using the present catalyst and include the conversion of chlorofluoromethane ($CH_2ClF$ or HCFC-31) into difluoromethane ($CH_2F_2$ or HFC-32) and dichloromethane ($CH_2Cl_2$ or HCC-30), the conversion of 1-chloro-1,1-difluoroethane ($CH_3CClF_2$ or HCFC-142b) into 1,1,1-trifluoroethane ($CH_3CF_3$ or HFC-143a) and 1,1-dichloro-1-fluoroethane ($CH_3CCl_2F$ or HCFC-141b), the conversion of 1-chloro-1,2,2,2-tetrafluoroethane ($CF_3CHClF$ or HCFC-124) into pentafluoroethane ($CF_3CHF_2$ or HFC-125) and into 2,2-dichloro-1,1,1-trifluoroethane ($CF_3CHCl_2$ or HCFC-123), the conversion of 1,1,3-trichloro-2,2,3,3-tetrafluoropropane ($CHCl_2CF_2CF_2Cl$ or HCFC-224ca) into 1,1-dichloro-2,2,3,3,3-pentafluoropropane ($CHCl_2CF_2CF_3$ or HCFC-225ca) and 1,1,3,3-tetrachloro-1,2,2-trifluoropropane ($CHCl_2CF_2CCl_2F$ or HCFC-223ca), the conversion of 1,1,1,3-tetrafluoro-3-chloropropane ($CF_3CH_2CHClF$ or HCFC-244fa) into 1,1,1,3,3-pentafluoropropane ($CHF_2CH_2CF_3$ or HFC-245fa) and into 1,1,1-trifluoro-3,3-dichloropropane ($CF_3CH_2CHCl_2$ or HCFC-243fa), the conversion of 1,1,2,3-tetrafluoro-1-chloropropane ($CF_2ClCHFCH_2F$ or HCFC-244ec) into 1,1,1,2,3-pentafluoropropane ($CF_3CHFCH_2F$ or HFC-245eb) and into 1,2,3-trifluoro-1,1-dichloropropane ($CFCl_2CHFCH_2F$ or HCFC-243ed), the conversion of 1,1,2,2-tetrafluoro-1-chloropropane ($CF_2ClCF_2CH_3$ or HCFC-244cc) into 1,1,1,2,2-pentafluoropropane ($CF_3CF_2CH_3$ or HFC-245cb) and 1,2,2-trifluoro-1,1-dichloropropane ($CFCl_2CF_2CH_3$ or HCFC-243cc), the conversion of 3-chloro-2,3,3-trifluoro-1-propene ($CH_2=CFCClF_2$ or HCFO-1233yf) into 2,3,3,3-tetrafluoropropene ($CF_3CF=CH_2$ or HFO-1234yf) and into 3,3-dichloro-2,3-difluoro-1-propene ($CH_2=CFCFCl_2$ or HCFO-1232yf) and the conversion of 3-chloro-1,3,3-trifluoro-1-propene ($CHF=CHCClF_2$ or HCFO-1233ze) into 1,3,3,3-tetrafluoropropene ($CHF=CHCF_3$ or HFO-1234ze) and 3,3-dichloro-1,3-difluoro-1-propene ($CHF=CHCCl_2F$ or HCFO-1232ze).

In a fifth implementation, the fluorine content of the hydrocarbon compound is decreased by reacting the said hydrocarbon compound with hydrogen chloride in the gas phase in the presence of the said solid composition, the said hydrocarbon compound being a halogenated hydrocarbon compound. This process is carried out in the presence of a catalyst which is a solid composition comprising at least one component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20%, advantageously of less than 15%, preferably of less than 10%, more preferably of less than 5%, ideally of less than 1%, by weight; in particular, the said solid composition is amorphous.

Preferably, the component containing chromium oxyfluoride or fluoride can be of empirical formula $Cr_xM_{(1-x)}O_rF_s$, where r is greater than or equal to 0 and less than 2.62, s is greater than or equal to $[(0.16\ r)+0.52]/0.92$, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to $[(0.24\ r)+0.78]/0.88$, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to $[(0.32\ r)+1.04]/0.84$, provided that s is greater than or equal to 1.52 and less than 6, more ideally still the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3]/0.8$, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to [(0.56 r)+1.82)]/0.72, provided that s is greater than or equal to 2.50 and less than 6. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above.

In particular, the said component containing chromium oxyfluoride or fluoride is a component containing chromium fluoride, preferably $CrF_3$, more preferably an amorphous $CrF_3$, ideally an anhydrous amorphous $CrF_3$.

In a preferred implementation, the solid composition comprises a support chosen from the group consisting of activated carbon, alumina and aluminium fluoride. Preferably, the solid composition has a specific surface between 1 and 100 $m^2/g$, preferably from 5 to 80 $m^2/g$, more preferably from 5 to 70 $m^2/g$, ideally from 5 to 50 $m^2/g$, in particular from 10 to 50 $m^2/g$, more particularly from 15 to 45 $m^2/g$.

In particular, the component containing chromium oxyfluoride or fluoride is of empirical formula $Cr_xM_{(1-x)}O_rF_s$, where r is greater than or equal to 0 and less than 2.05, s is greater than or equal to [(0.4 r)+1.3)]/0.8, provided that s is greater than or equal to 1.90 and less than 6, preferably of empirical formula $Cr_xM_{(1-x)}O_rF_s$, where r is greater than or equal to 0 and less than 1.75, s is greater than or equal to [(0.56 r)+1.82)]/0.72, provided that s is greater than or equal to 2.50 and less than 6, and with a specific surface between 10 and 50 $m^2/g$. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above and with a specific surface between 10 and 50 $m^2/g$.

The fluorinated hydrocarbon compounds appropriate as starting materials for the process of this implementation can be saturated or unsaturated. The saturated halogenated hydrocarbon compounds appropriate for the chlorodefluorination processes according to this invention include those of general formula $C_nH_aCl_cF_d$, where n is an integer between 1 and 6, a is an integer between 0 and 13, c is an integer between 0 and 13, d is an integer between 1 and 13, and the sum of a, c and d is equal to 2n+2. The unsaturated halogenated hydrocarbon compounds appropriate for the chlorodefluorination processes according to this invention include those of general formula $C_pH_eCl_gF_h$, where p is an integer between 2 and 6, e is an integer between 0 and 11, g is an integer between 0 and 12, h is an integer between 1 and 11, and the sum of e, g and h is equal to 2p.

The chlorodefluorination reactions are typically carried out at temperatures of approximately 250° C. to 450° C., preferably of approximately 300° C. to approximately 400° C. The contacting time in the reactor is typically from approximately 1 to approximately 120 s. Of course, contact times of approximately 5 to approximately 60 s are possible. The reactions are ideally carried out at atmospheric or greater pressure.

The chlorodefluorinations involving saturated halogenated hydrocarbons are particularly worthy of interest. The molar ratio of HCl to the saturated halogenated hydrocarbon compound typically lies between approximately 1:1 and approximately 100:1, preferably from approximately 3:1 to approximately 50:1, and ideally from approximately 4:1 to approximately 30:1. In general, with a given catalytic composition, the greater the temperature, the greater the contact time, the greater the molar ratio of HCl to the saturated halogenated hydrocarbon compound and the greater the conversion of the compounds having a low fluorine content.

The above variables can be balanced with respect to one another in order to maximize the formation of chlorinated products.

The product of the chlorodefluorination reactions typically comprises HCl and unreacted HF, unconverted starting material and saturated halogenated hydrocarbon compounds having a lower fluorine content than the starting material as a result of the substitution of one or more fluorine substituents by chlorine.

The reaction products obtained by the processes described in detail in any one of the first five implementations can be separated by conventional techniques, such as with combinations including, nonlimitingly, washing, settling or distillation. Some of the products of the various implementations of this invention can form one or more azeotropes with one another or with HF.

The processes disclosed in the present invention can include, in addition, the stage of regeneration of the said solid composition in the presence of a regeneration stream comprising a stream of air/oxidant. The oxidant can be oxygen, air, a mixture of oxygen and nitrogen, chlorine or a mixture of chlorine and nitrogen. When the regeneration is carried out with air or a mixture of oxygen and nitrogen, the proportion of oxygen can range from 5 mol % to 100 mol %, with respect to the mixture of oxygen and nitrogen.

The regeneration stage can be carried out in the presence of a regeneration stream containing (a) oxygen or air or an oxygen/nitrogen mixture or chlorine and (b) HF.

Advantageously, the regeneration stream will contain at least 1 mol % of oxygen, with respect to the total regeneration stream. The proportion of oxygen can range from 2 mol % to 98 mol %, with respect to the total amount expressed in moles of oxygen and HF, and from 20 mol % to 100 mol %, with respect to the total amount expressed in moles of oxygen and nitrogen.

The regeneration stage is successfully carried out at a temperature of 250 to 500° C., preferably of 300 to 450° C., more preferably of 350 to 400° C. The regeneration stage can be successfully carried out with a contact time of 1 to 200 s, preferably of 1 to 150 s, more preferably of 5 to 100 s, and for a period of time of 1 to 1500 h, preferably of 2 to 1000 h, more preferably of 4 to 500 h, ideally of 10 to 200 h and in particular of 15 to 150 h. The regeneration stage can be successfully carried out under a pressure ranging from atmospheric pressure to 20 bar. In particular, the regeneration stage can be successfully carried out at a temperature of 250 to 500° C., with a contact time of 1 to 200 s, for 10 to 200 h and under a pressure between atmospheric pressure and 20 bar.

The processes disclosed in the present invention can comprise, in addition, the stage of activation of the said solid composition in the presence of an air/oxidant stream.

Before use, it is preferable for the catalyst to be subjected to a stage of activation with air, oxygen or chlorine and/or HF. For example, the catalyst is preferably subjected to an activation with air or oxygen and HF at a temperature between 100 and 500° C., preferably between 250 and 500° C. and in particular between 300 and 400° C. The duration of activation is preferably from 1 to 200 h and in particular from 1 to 50 h. This activation can be followed by a final stage of fluorination activation in the presence of an oxidant, HF and hydrocarbon compounds. The HF/hydrocarbon compound molar ratio ranges from 2 to 40 and the oxidant/hydrocarbon compound molar ratio ranges from 0.04 to 25. The temperature of the final stage of fluorination activation can range from 300 to 400° C., preferably for a duration of 6 to 100 h.

Otherwise, the present invention can also provide a process for modifying the distribution of chlorine in a hydrocarbon compound in the presence of a catalyst, characterized by the use, as catalyst, of a solid composition comprising at least one component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20%. The chlorine content of the hydrocarbon compound is reduced by dehydrochlorination of the said hydrocarbon compound in the presence of the said solid composition, the said hydrocarbon compound being a chlorinated hydrocarbon compound. The chlorinated hydrocarbon compounds appropriate as starting materials for the dehydrochlorination process are typically saturated. The saturated chlorinated hydrocarbon compounds include those of general formula $C_nH_aCl_d$, where n is an integer between 2 and 6, a is an integer between 1 and 12, d is an integer between 1 and 13, and the sum of a and d is equal to 2n+2. The chlorine content of the saturated compounds of formula $C_nH_aCl_d$ can be reduced in the presence of a catalyst which is a solid composition comprising at least one component containing chromium oxyfluoride or fluoride of empirical formula $Cr_xM_{(1-x)}O_rF_s$, where 2r+s is greater than or equal to 3 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20%, advantageously of less than 15%, preferably of less than 10%, more preferably of less than 5%, ideally of less than 1%, by weight; in particular, the said solid composition is amorphous. Preferably, the component containing chromium oxyfluoride or fluoride can be of empirical formula $Cr_xM_{(1-x)}O_rF_s$, where r is greater than or equal to 0 and less than 2.62, s is greater than or equal to $[(0.16 r)+0.52)]/0.92$, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to $[(0.24 r)+0.78)]/0.88$, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to $[(0.32 r)+1.04)]/0.84$, provided that s is greater than or equal to 1.52 and less than 6, more ideally still the component containing chromium oxyfluoride or fluoride is of empirical formula $Cr_xM_{(1-x)}O_rF_s$, where r is greater than or equal to 0 and less than 2.05, s is greater than or equal to $[(0.4 r)+1.3)]/0.8$, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to $[(0.56 r)+1.82)]/0.72$, provided that s is greater than or equal to 2.50 and less than 6. The component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above.

In particular, the said component containing chromium oxyfluoride or fluoride is a component containing chromium fluoride, preferably $CrF_3$, more preferably an amorphous $CrF_3$, ideally an anhydrous amorphous $CrF_3$. In a preferred implementation, the solid composition comprises a support chosen from the group consisting of activated carbon, alumina and aluminium fluoride. Preferably, the solid composition has a specific surface between 1 and 100 m$^2$/g, preferably between 5 and 80 m$^2$/g, more preferably between 5 and 70 m$^2$/g, ideally between 5 and 50 m$^2$/g, in particular from 10 to 50 m$^2$/g, more particularly from 15 to 45 m$^2$/g. In particular, the component containing chromium oxyfluoride or fluoride is of empirical formula $Cr_xM_{(1-x)}O_rF_s$, where r is greater than or equal to 0 and less than 2.05, s is greater than or equal to $[(0.4 r)+1.3)]/0.8$, provided that s is greater than or equal to 1.90 and less than 6, preferably of empirical formula $Cr_xM_{(1-x)}O_rF_s$, where r is greater than or equal to 0 and less than 1.75, s is greater than or equal to $[(0.56 r)+1.82)]/0.72$, provided that s is greater than or equal to 2.50 and less than 6, and with a specific surface between 10 and 50 m$^2$/g. The component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above and a specific surface between 10 and 50 m$^2$/g.

The process according to this alternative implementation can be carried out in a reactor comprising a catalytic bed containing a catalyst and according to the following operating conditions:

contact time of 1 to 100 s, preferably of 2 to 75 s, in particular of 3 to 50 s;

pressure between atmospheric pressure and 20 bar, preferably from 2 to 18 bar, more preferably from 3 to 15 bar;

temperature (of the catalytic bed) of 200 to 450° C., preferably of 250 to 400° C., more preferably of 280 to 380° C.

The process can be carried out for a period of time of 10 to 8000 h, preferably of 50 to 5000 h, more preferably of 70 to 1000 h. The process is typically carried out in a tubular reactor. The reactor and its associated feed lines, effluent lines and associated devices have to be constructed from materials which are resistant to hydrogen fluoride and to hydrogen chloride. Typical construction materials, well known in the state of the art of fluorination, include stainless steels, in particular of austenitic type, well-known alloys having a high nickel content, such as Monel® nickel/copper alloys, Hastelloy® nickel-based alloys and Inconel® nickel/chromium alloys.

The product of the dehydrochlorination reaction consists of HCl and the unsaturated fluorinated hydrocarbon compound resulting from the loss of HCl by the initial reactant. Specific examples of vapour-phase dehydrochlorination reactions which can be carried out by using the catalysts of this invention include the conversion of 1-chloro-2,2-difluoroethane ($CH_2ClCF_2H$ or HCFC-142) into 1,1-difluoroethylene ($CH_2=CF_2$ or HFO-1132a), the conversion of 1,1,1,3-tetrafluoro-3-chloropropane ($CF_3CH_2CHClF$ or HCFC-244fa) into 1,3,3,3-tetrafluoropropene ($CHF=CHCF_3$ or HFO-1234ze), the conversion of 1,1,1-trifluoro-3,3-dichloropropane ($CF_3CH_2CHCl_2$ or HCFC-243fa) into 1-chloro-3,3,3-trifluoro-1-propene ($CHCl=CHCF_3$ or HFO-1233zd), the conversion of 2,3-dichloro-1,1,1-trifluoropropane ($CF_3CHClCH_2Cl$ or HCFC-243db) into 2-chloro-3,3,3-trifluoro-1-propene ($CF_3CCl=CH_2$ or HFCO-1233xf), the conversion of 2-chloro-1,1,1,2-tetrafluoropropane ($CF_3CFClCH_3$ or HCFC-244bb) into 2,3,3,3-tetrafluoropropene ($CF_3CF=CH_2$ or HFO-1234yf) and the conversion of 1,1,1,4,4,4-hexafluoro-2-chlorobutane ($CF_3CHClCH_2CF_3$ or HFC-346mdf) into 1,1,1,4,4,4-hexafluoro-2-butene ($CF_3CH=CHCF_3$ or HFO-1336mzz). The process for modifying the chlorine distribution in a hydrocarbon compound can successfully be carried out simultaneously with a process for modifying the fluorine distribution in another hydrocarbon compound, for example by increasing or reducing the fluorine content in the said other hydrocarbon compound, as described in detail above with reference to the first embodiment and the second embodiment. Consequently, the conversion of 2-chloro-1,1,1,2-tetrafluoropropane ($CF_3CFClCH_3$ or HCFC-244bb) into 2,3,3,3-tetrafluoropropene ($CF_3CF=CH_2$ or HFO-1234yf) can be carried out with the present solid composition simultaneously with the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf).

In a sixth implementation, the fluorine content of a first hydrocarbon compound is increased by reacting the said first hydrocarbon compound with hydrogen fluoride in the gas phase in the presence of a solid composition, the first hydrocarbon compound being a saturated halogenated hydrocarbon or an unsaturated halogenated hydrocarbon or an unsaturated hydrocarbon, and the fluorine content of a second hydrocarbon compound is reduced by dehydrofluorinating the said second hydrocarbon compound in the presence of the said solid composition, the said second hydrocarbon compound being a fluorinated hydrocarbon compound. The first hydrocarbon compound, which is a saturated halogenated hydrocarbon or an unsaturated halogenated hydrocarbon or an unsaturated hydrocarbon, is defined above with reference to the first implementation. The second hydrocarbon compound is defined above with reference to the second implementation. The fluorination of the first hydrocarbon compound and the dehydrofluorination of the second hydrocarbon compound are preferably carried out simultaneously.

The solid composition comprises at least one component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20%, by weight, advantageously of less than 15%, preferably of less than 10%, more preferably of less than 5%, ideally of less than 1%, by weight; in particular, the said solid composition is amorphous.

Preferably, the component containing chromium oxyfluoride or fluoride can be of empirical formula $Cr_xM_{(1-x)}O_rF_s$, where r is greater than or equal to 0 and less than 2.62, s is greater than or equal to [(0.16 r)+0.52)]/0.92, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to [(0.24 r)+0.78)]/0.88, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to [(0.32 r)+1.04)]/0.84, provided that s is greater than or equal to 1.52 and less than 6, more ideally still the component containing chromium oxyfluoride or fluoride is of empirical formula $Cr_xM_{(1-x)}O_rF_s$, where r is greater than or equal to 0 and less than 2.05, s is greater than or equal to [(0.4 r)+1.3)]/0.8, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to [(0.56 r)+1.82)]/0.72, provided that s is greater than or equal to 2.50 and less than 6. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above.

In particular, the said component containing chromium oxyfluoride or fluoride is a component containing chromium fluoride, preferably $CrF_3$, more preferably an amorphous $CrF_3$, ideally an anhydrous amorphous $CrF_3$.

In a preferred implementation, the solid composition comprises a support chosen from the group consisting of activated carbon, alumina and aluminium fluoride. Preferably, the solid composition has a specific surface between 1 and 100 $m^2/g$, preferably between 5 and 80 $m^2/g$, more preferably between 5 and 70 $m^2/g$, ideally between 5 and 50 $m^2/g$, in particular from 10 to 50 $m^2/g$, more particularly from 15 to 45 $m^2/g$.

In particular, the component containing chromium oxyfluoride or fluoride is of empirical formula $Cr_xM_{(1-x)}O_rF_s$, where r is greater than or equal to 0 and less than 2.05, s is greater than or equal to [(0.4 r)+1.3)]/0.8, provided that s is greater than or equal to 1.90 and less than 6, preferably of empirical formula $Cr_xM_{(1-x)}O_rF_s$, where r is greater than or equal to 0 and less than 1.75, s is greater than or equal to [(0.56 r)+1.82)]/0.72, provided that s is greater than or equal to 2.50 and less than 6, and with a specific surface between 10 and 50 $m^2/g$. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above and with a specific surface between 10 and 50 $m^2/g$.

The process according to the sixth implementation can be carried out in a reactor comprising a catalytic bed containing a catalyst and according to the following operating conditions:

an HF/hydrocarbon compound molar ratio of 1:1 to 150:1, preferably of 2:1 to 125:1, more preferably of 3:1 to 100:1;

a contact time of 1 to 100 s, preferably of 2 to 75 s, in particular of 3 to 50 s;

a pressure between atmospheric pressure and 20 bar, preferably between 2 and 18 bar, more preferably between 3 and 15 bar;

a temperature (of the catalytic bed) between 200 and 450° C., preferably between 250 and 400° C., more preferably between 280° C. and 380° C.

The process can be successfully carried out over a period of time of between 10 and 8000 h, preferably between 50 and 5000 h, more preferably between 70 and 1000 h.

An oxidant, such as oxygen or chlorine, can be added during the process. The molar ratio of the oxidant to the hydrocarbon compound can be between 0.005 and 2, preferably between 0.01 and 1.5. The oxidant can be pure oxygen, air or a mixture of oxygen and nitrogen.

The process is typically carried out in a tubular reactor. The reactor and its associated feed lines, effluent lines and associated devices have to be constructed from materials which are resistant to hydrogen fluoride and to hydrogen chloride. Typical construction materials, well known in the state of the art of fluorination, include stainless steels, in particular of austenitic type, well-known alloys having a high nickel content, such as Monel® nickel/copper alloys, Hastelloy® nickel-based alloys and Inconel® nickel/chromium alloys.

The products of the reaction are those described in detail with reference to the first embodiment and the second embodiment. In particular, the solid composition is of use for the conversion of 1,1,1,2,3-pentachloropropane ($CCl_3CHClCH_2Cl$ or HCC-240db) into 2-chloro-3,3,3-trifluoro-1-propene ($CF_3CCl=CH_2$ or HCFO-1233xf) or the conversion of 1,1,1,2,3-pentachloropropane ($CCl_3CHClCH_2Cl$ or HCC-240db) into 2,3,3,3-tetrafluoropropene ($CF_3CF=CH_2$ or HFO-1234yf) or the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf) and the conversion of 1,1,1,2,2-pentafluoropropane ($CF_3CF_2CH_3$ or HFC-245cb) into 2,3,3,3-tetrafluoropropene ($CF_3CF=CH_2$ or HFO-1234yf) or the conversion of 1,1,1,2,3-pentafluoropropane ($CF_3CHFCH_2F$ or HFC-245eb) into 2,3,3,3-tetrafluoropropene ($CF_3CF=CH_2$ or HFO-1234yf). In particular, the solid composition is of use for the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf) and the conversion of 1,1,1,2,2-pentafluoropropane ($CF_3CF_2CH_3$ or HFC-245cb) into 2,3,3,3-tetrafluoropropene ($CF_3CF=CH_2$ or HFO-1234yf).

In a seventh implementation, the fluorine content of a first hydrocarbon compound is increased by reacting the said first hydrocarbon compound with hydrogen fluoride in the gas phase in the presence of a solid composition, the first hydrocarbon compound being a saturated halogenated hydrocarbon or an unsaturated halogenated hydrocarbon or an unsaturated hydrocarbon, and the chlorine content of a second hydrocarbon compound is reduced by dehydrochlorinating the said second hydrocarbon compound in the presence of the said solid composition, the said second hydrocarbon compound being a fluorinated hydrocarbon compound.

In this embodiment, the solid composition according to the present invention is of use for the conversion of 2-chloro-3,3,3-trifluoro-1-propene ($CF_3CCl=CH_2$ or HCFO-1233xf) into 2,3,3,3-tetrafluoropropene ($CF_3CF=CH_2$ or HFO-1234yf) and the conversion of 2-chloro-1,1,1,2-tetrafluoropropane ($CF_3CFClCH_3$ or HCFO-244bb) into 2,3,3,3-tetrafluoropropene ($CF_3CF=CH_2$ or HFO-1234yf).

The solid composition comprises at least one component containing chromium oxyfluoride or fluoride of empirical formula $Cr_xM_{(1-x)}O_rF_s$, where $2r+s$ is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20%, by weight, advantageously of less than 15%, preferably of less than 10%, more preferably of less than 5%, ideally of less than 1%, by weight; in particular, the said solid composition is amorphous.

Preferably, the component containing chromium oxyfluoride or fluoride can be of empirical formula $Cr_xM_{(1-x)}O_rF_s$, where r is greater than or equal to 0 and less than 2.62, s is greater than or equal to $[(0.16\ r)+0.52)]/0.92$, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to $[(0.24\ r)+0.78)]/0.88$, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to $[(0.32\ r)+1.04)]/0.84$, provided that s is greater than or equal to 1.52 and less than 6, more ideally still the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3)]/0.8$, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above.

In particular, the said component containing chromium oxyfluoride or fluoride is a component containing chromium fluoride, preferably $CrF_3$, more preferably an amorphous $CrF_3$, ideally an anhydrous amorphous $CrF_3$.

In a preferred implementation, the solid composition comprises a support chosen from the group consisting of activated carbon, alumina and aluminium fluoride. Preferably, the solid composition has a specific surface between 1 and 100 $m^2/g$, preferably between 5 and 80 $m^2/g$, more preferably between 5 and 70 $m^2/g$, ideally between 5 and 50 $m^2/g$, in particular from 10 to 50 $m^2/g$, more particularly from 15 to 45 $m^2/g$.

In particular, the component containing chromium oxyfluoride or fluoride is of empirical formula $Cr_xM_{(1-x)}O_rF_s$, where r is greater than or equal to 0 and less than 2.05, s is greater than or equal to $[(0.4\ r)+1.3)]/0.8$, provided that s is greater than or equal to 1.90 and less than 6, preferably of empirical formula $Cr_xM_{(1-x)}O_rF_s$, where r is greater than or equal to 0 and less than 1.75, s is greater than or equal to $[(0.56\ r)+1.82)]/0.72$, provided that s is greater than or equal to 2.50 and less than 6, and with a specific surface between 10 and 50 $m^2/g$. In particular, M is zinc. Consequently, the component containing chromium oxyfluoride or fluoride can be of empirical formula $Cr_xZn_{(1-x)}O_rF_s$, where x has a value between 0.9 and 1, preferably between 0.9 and 0.999, more preferably between 0.94 and 0.99, with r and s as defined above and a specific surface between 10 and 50 $m^2/g$.

The process according to the seventh implementation can be carried out in a reactor comprising a catalytic bed containing a catalyst and according to the following operating conditions:
- an HF/hydrocarbon compound molar ratio of 1:1 to 150:1, preferably of 2:1 to 125:1, more preferably of 3:1 to 100:1;
- a contact time of 1 to 100 s, preferably of 2 to 75 s, in particular of 3 to 50 s;
- a pressure between atmospheric pressure and 20 bar, preferably between 2 and 18 bar, more preferably between 3 and 15 bar;
- a temperature (of the catalytic bed) between 200 and 450° C., preferably between 250 and 400° C., more preferably between 280° C. and 380° C.

The process can be successfully carried out over a period of time of between 10 and 8000 h, preferably between 50 and 5000 h, more preferably between 70 and 1000 h.

In a second aspect of the present invention, there is produced a solid composition, the said solid composition comprising a component containing chromium oxyfluoride or fluoride of empirical formula $Cr_xM_{(1-x)}O_rF_s$, where 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid catalytic composition having a crystallinity of less than 20% by weight.

In a preferred embodiment, the said solid composition has a crystallinity of less than 15%, preferably of less than 10%, more preferably of less than 5%, ideally of less than 1%, by weight; in particular, the said solid composition is amorphous.

In a preferred implementation, the said component containing chromium oxyfluoride or fluoride is of empirical formula $Cr_xM_{(1-x)}O_rF_s$, where M is chosen from the group consisting of Zn, Mg, Co, Mn and Ni, preferably Zn; in particular, x has a value between 0.9 and 1, preferably between 0.9 and 0.999, more preferably between 0.94 and 0.99.

Preferably, the component containing chromium oxyfluoride or fluoride can be of empirical formula $Cr_xM_{(1-x)}O_rF_s$, where r is greater than or equal to 0 and less than 2.62, s is greater than or equal to [(0.16 r)+0.52)]/0.92, provided that s is greater than or equal to 0.76 and less than 6, more preferably the component containing chromium oxyfluoride or fluoride is of empirical formula $Cr_xM_{(1-x)}O_rF_s$, where r is greater than or equal to 0 and less than 2.43, s is greater than or equal to [(0.24 r)+0.78)]/0.88, provided that s is greater than or equal to 1.14 and less than 6, ideally the component containing chromium oxyfluoride or fluoride is of empirical formula $Cr_xM_{(1-x)}O_rF_s$, where r is greater than or equal to 0 and less than 2.24, s is greater than or equal to [(0.32 r)+1.04)]/0.84, provided that s is greater than or equal to 1.52 and less than 6, more ideally still the component containing chromium oxyfluoride or fluoride is of empirical formula $Cr_xM_{(1-x)}O_rF_s$, where r is greater than or equal to 0 and less than 2.05, s is greater than or equal to [(0.4 r)+1.3)]/0.8, provided that s is greater than or equal to 1.90 and less than 6, in particular the component containing chromium oxyfluoride or fluoride is of empirical formula $Cr_xM_{(1-x)}O_rF_s$, where r is greater than or equal to 0 and less than 1.75, s is greater than or equal to [(0.56 r)+1.82)]/0.72, provided that s is greater than or equal to 2.50 and less than 6. In particular, in the above formula, M is zinc and x has a value between 0.9 and 1, preferably between 0.9 and 0.999, more preferably between 0.94 and 0.99. Preferably, the component containing chromium oxyfluoride or fluoride is amorphous and/or anhydrous.

In a preferred embodiment, the component containing chromium is a component containing chromium fluoride, preferably $CrF_3$ or $Cr_xZn_xF_3$, more preferably an amorphous $CrF_3$ or $Cr_xZn_xF_3$, ideally an anhydrous amorphous $CrF_3$ or $Cr_xZn_xF_3$, where x has a value between 0.9 and 1, preferably between 0.9 and 0.999, more preferably between 0.94 and 0.99.

In a third aspect of the present invention, the use of a solid catalytic composition in a process carried out in the presence of HF is revealed.

In a fourth aspect, the present invention provides a process for the preparation of a solid catalytic composition according to the present invention. The said process comprises:
(a) a reaction stage which comprises bringing a chromium oxide component, in the presence of hydrogen fluoride, and a halogenated hydrocarbon compound into contact at a temperature of 200 to 450° C. for at least 100 h, in order to form a dedicated chromium oxide component,
(b) a stage of regeneration of the dedicated chromium oxide in the presence of a gas stream of an oxidant, preferably of air, at a temperature of 250 to 500° C. for at least 1 h, preferably at least, in order to form a regenerated chromium oxide component,
c) the repetition, at least twice, of stages (a) and (b) with the regenerated chromium oxide until the said regenerated chromium oxide component has become a component containing chromium oxyfluoride or fluoride of empirical formula $Cr_xM_{(1-x)}O_rF_s$, in which 2r+s is greater than or equal to 2.9 and less than 6, M is a metal chosen from columns 2 to 12 of the Periodic Table of the Elements, x has a value between 0.9 and 1, s is greater than 0 and less than or equal to 6 and r is greater than or equal to 0 and less than 3, the said solid composition having a crystallinity of less than 20% by weight. Preferably, the said chromium oxide component is an amorphous chromium oxide component.

EXAMPLES

Process for the Quantification of the Crystallinity:

The crystallinity is determined as a function of the result of an X-ray crystallography measurement. Specifically, the crystallinity denotes the ratio determined by the comparison between the surface area of the diffraction peaks of all the crystalline planes of the standard sample with that of the target component containing chromium oxyfluoride or fluoride, each surface area being calculated from a diffraction diagram obtained by X-ray crystallography measurement under the same conditions. Components of known crystallinity were analysed in order to prepare a calibration curve, from which it is possible to determine the crystallinity of the component containing chromium oxyfluoride or fluoride Examples 1 and 2

Fluorination of 1,1,1,2,3-pentachloropropane ($CCl_3CHClCH_2Cl$ or HCC-240db)

The equipment consists of two multitubular reactors in series, each tube having an internal diameter of 28 mm, manufactured from Inconel® alloy 600 steel. The process carried out in Examples 1 and 2 is represented in the Figure.

The first gas-phase reactor 3 is fed with fresh HCC-240db via the line 2, and optionally with fresh HF via the line 1. The reaction mixture 4 which leaves the reactor contains HCl, HCFO-1233xf, unreacted HF, HFO-1234yf and optionally HFC-245cb. This reaction stream is separated by distillation 5 into a first stream 6 containing HCl, HFO-1234yf, optionally with a small amount of HF and minor amounts of HFC-245cb and HFO-1233xf. A heavier second stream 7 is obtained at the bottom of the distillation column, which stream contains HF, HCFO-1233xf, HFC-245cb. It is possible to separate and purify HFO-1234yf from the stream 6 by using known processes.

The second reactor 10 is fed with the stream 9 which consists of the second stream 7, optionally with fresh HF 8. The reaction mixture 11 which leaves the reactor contains HCl, unreacted HCFO-1233xf, unreacted HF, HFO-1234yf, HFC-245cb. This reaction mixture is sent directly to the first reactor without being subjected to any separation.

The catalyst is an amorphous mass of chromium oxide $Cr_2O_3$ activated with 2% by weight of zinc, containing approximately 4% of graphite. The reactor is equipped with a pressure and temperature controller. At the outlet of the reactor, the products of the reaction are washed through a KOH scrubber in order to remove the hydracids. Several samples are withdrawn for in-line analysis by gas chromatography: inlet of the first reactor, outlet of the first reactor, outlet of the second reactor and final product at the top of the distillation column. Two different GC analyses are necessary in order to detect the huge range of possible products. The chromatographic analysis is carried out on an RTX 200 column in order to quantify a broad range of organic products, dimensions 105 m×0.32 mm×2 µm. The programming of the temperature of the oven is as follows: 40° C. for 10 min, then slope of 10° C./min up to 300° C. The chromatographic analysis is carried out on a Shincarbon 2 m×1.8" column for a quantification and a better separation of the lightest products and also of the inert products (CO, $CO_2$, $O_2$). The programming of the temperature of the oven is as follows: 40° C. for 10 min, then slope of 10° C./min up to 300° C.

Example 1

The catalyst was prefluorinated before reaction. The prefluorination was carried out by carrying out a fluorination reaction for 100 h under the following conditions: T=350° C., P=5 bar, with an HF/organic molar ratio of 15 to 30, alternatively with a regeneration stage carried out with air at 360° C. The reaction and regeneration stages are repeated. The catalyst $Cr_xZn_{(1-x)}O_rF_s$ was analysed before use: s=1.7 and r=0.7, x=0.97 and the specific surface was approximately 42 m²/g. The catalyst is amorphous. The fluorination reaction is subsequently carried out at T=350° C. under an absolute pressure of 5 bar. The feeding with fresh HF was 1.6 kg/h, and the stream of chlorinated compound was approximately 4 kg/h. The flow rate of the recycling loop was 34 kg/h, which gives a contact time with regard to the first reactor of approximately 15 s. The HF/organic molar ratio is between 15 and 20: it corresponds to the ratio of HF to the sum of the organic compounds. The results are given in Table 1 below. Good selectivities are obtained throughout the experiment.

Example 2

The catalyst was prefluorinated before reaction. The prefluorination was carried out by carrying out a fluorination reaction for 840 h under the following conditions: T=350° C., P=5 bar, with an HF/organic molar ratio of 15 to 30, alternatively with a regeneration stage carried out with air at 360° C. The catalyst $Cr_xZn_{(1-x)}O_rF_s$ was analysed before use: s=3.0 and r=0.17, x=0.98 and the specific surface was approximately 22 m²/g. The catalyst is amorphous. The fluorination reaction is subsequently carried out at T=350° C. under an absolute pressure of 5 bar. The feeding with fresh HF was 1.7 kg/h, and the stream of chlorinated compound was approximately 3.9 kg/h. The flow rate of the recycling loop was 34 kg/h, which gives a contact time with regard to the first reactor of approximately 15 s. The HF/organic molar ratio is between 15 and 20: it corresponds to the ratio of HF to the sum of the organic compounds. The results are given in Table 1 below. Good selectivities are obtained throughout the experiment.

TABLE 1

| Flow time (h) | Conversion of HCFO-F1233xf in the reactor (10) Example 1 | Flow time (h) | Conversion of HCFO-F1233xf in the reactor (10) Example 2 |
| --- | --- | --- | --- |
| 2.2 | 70.9 (%) | 15.0 | 73.1 (%) |
| 18.5 | 56.8 (%) | 90.8 | 69.9 (%) |
| 26.0 | 50.6 (%) | 153.1 | 66.7 (%) |
| 34.2 | 52.3 (%) | 235.0 | 62.1 (%) |
| 42.3 | 47.7 (%) | 315.9 | 57.2 (%) |
| 50.5 | 42.9 (%) | 389.0 | 50.9 (%) |
| 58.7 | 42.9 (%) | 421.4 | 47.8 (%) |
| 66.8 | 39.5 (%) | 453.9 | 42.7 (%) |
| 74.8 | 35.8 (%) | 495.0 | 37.1 (%) |

Example 3

Isomerization of 1,1,1,2,3-pentafluoropropane ($CF_3CHFCH_2F$ or HFC-245eb)

The catalyst used in this example was a commercial bulk amorphous chromium catalyst. The catalyst was prefluorinated before reaction. The prefluorination was carried out by a fluorination reaction (R—Cl+HF→R—F+HCl) for 1000 h under the following conditions: T=350° C., P=3 bar and HF/organic between 20 and 30. The catalyst $CrO_rF_s$ was analysed before use: s=1.9 and r=0.54, and the specific surface was approximately 32 m²/g. A Hastelloy C (3/4"× 16") fixed bed reactor was charged with 23 cm³ of prefluorinated commercial bulk Cr catalyst. The catalyst was evaluated under atmospheric pressure at a temperature of 375° C. by using a mixture of HFC-245eb and nitrogen ($N_2$/HFC-245eb molar ratio=1.4). The feeding conditions correspond to a contact time of 9 s. The organic product obtained from the reactor was washed, dried and analysed by gas chromatography. An excellent conversion of HFC-245eb was observed with a promising selectivity for 1,1,1,2,2-pentafluoropropane ($CF_3CF_2CH_3$ or HFC-245cb).

Example 4

Dehydrofluorination of 1,1,1,3,3-pentafluoropropane ($CHF_2CH_2CF_3$ or HFC-245fa)

The catalyst of Example 3 was used to dehydrofluorinate HFC-245fa in a similar reactor to that described in Example 3. 20 cm³ of the prefluorinated commercial bulk amorphous chromium catalyst. The catalyst was evaluated under atmospheric pressure at a temperature of 400° C. by using a mixture of HFC-245fa and air (equal to approximately 3% by volume of oxygen, with respect to the volume of HFC-245fa). The feeding conditions correspond to a contact time of 40 s. The conversion of HFC-245fa was greater than 90%, with an excellent selectivity for 1,3,3,3-tetrafluoropropene ($CHF=CHCF_3$ or HFO-1234ze) (greater than 90%).

Example 5

Fluorination of 1,1,2-trichloroethane ($CHCl_2CH_2Cl$ or HCC-140)

The catalyst used in this example was a commercial bulk amorphous chromium catalyst. The catalyst was prefluorinated before reaction by using a treatment with pure HF at T=350° C. until the desired compound is obtained. The catalyst $CrO_rF_s$ was analysed before use: s=1.8 and r=0.62, and the specific surface was approximately 46 m²/g. A monotubular reactor made of Inconel was charged with 40 g of pretreated Cr catalyst. The reactor was fitted inside a boiler, and the reaction region was maintained at 225° C. The pressure was maintained at approximately P=11 bar. The organic ($CHCl_2CH_2Cl$ or HCC-140), hydrogen fluoride and chlorine feed was introduced into the reactor in a molar ratio of 1:20:0.08. The HF rate was approximately 1.8 mol/h and the contact time was approximately 18 s. GC was used to analyse the effluent from the reactor. The desired product 1-chloro-2,2-difluoroethane ($CH_2ClCF_2H$ or HCFC-142) was obtained with a yield of 65%.

The invention claimed is:

1. A process for modifying the fluorine distribution in a hydrocarbon compound in the presence of a catalyst, the catalyst being a solid composition containing at least one component containing chromium oxyfluoride or fluoride of empirical formula $Cr_xM_{(1-x)}O_rF_s$, wherein 2r+s is greater than or equal to 2.9 and less than 6, M is a metal chosen from the group consisting of Zn, Mg, Co, Mn and Ni, x has a value from 0.9 to 0.999, s is greater than 0 and less than or equal to 6, and r is greater than or equal to 0 and less than 3, wherein the solid composition has a crystallinity of less than 20% by weight; and wherein the fluorine content of the hydrocarbon compound is increased by reacting the hydrocarbon compound with hydrogen fluoride in the gas phase in the presence of the solid composition, the hydrocarbon compound being a saturated halogenated hydrocarbon or an unsaturated halogenated hydrocarbon or an unsaturated hydrocarbon.

2. The process according to claim 1, wherein the solid composition has a crystallinity of less than 15%.

3. The process according to claim 1, wherein M is Zn.

4. The process according to claim 1, wherein the hydrocarbon compound is chosen from the group consisting of tetrachloropropene, chlorotrifluoropropene, pentachloropropane, dichlorotrifluoropropane, trichlorodifluoropropane, tetrafluorochloropropane, tetrachlorofluoropropane, dichlorodifluoropropene, trichlorofluoropropene, pentafluoropropane and their mixtures.

5. The process according to claim 4, wherein the hydrocarbon compound is chosen from the group consisting of 2 chloro-3,3,3-trifluoro-1-propene (HFCO-1233xf), 2,3-dichloro-1,1,1-trifluoropropane (HCFC-243db), 1,1,1,2,3-pentachloropropane (HCC-240db), 1,1,2,2,3-pentachloropropane (HCC-240aa), 1,1,1,3,3-pentachloropropane (HCC-240fa), 1,1,2,3-tetrachloro-1-propene (HCO-1230xa), 2,3,3,3-tetrachloro-1-propene (HCO-1230xf), 1,1,3,3-tetrachloro-1-propene (HCO-1230za), 1,3,3,3-tetrachloro-1-propene (HCO-1230zd), 1,1,1,2,2-pentafluoropropane (HFC-245cb) and 1-chloro-3,3,3-trifluoro-1-propene (HCFO-1233zd), and their mixtures.

6. The process according to claim 1, wherein the component containing chromium oxyfluoride or fluoride is of empirical formula $Cr_xM_{(1-x)}O_rF_s$, where r is greater than or equal to 0 and less than 2.62, s is greater than or equal to [((0.16 r)+0.52)]/0.92, on condition that s is greater than or equal to 0.76 and less than 6.

7. A process for modifying the fluorine distribution in a hydrocarbon compound in the presence of a catalyst, the catalyst being a solid composition containing at least one component containing chromium oxyfluoride or fluoride of empirical formula $Cr_xM_{(1-x)}O_rF_s$, Wherein 2r+s is greater than or equal to 2.9 and less than 6, M is a metal from columns 2 to 12 of the Periodic Table of the Elements, x has a value from 0.9 to 0.999,0078840-000366, s is greater than 0 and less than or equal to 6, and r is greater than or equal to 0 and less than 3, wherein the solid composition has a crystallinity of less than 20% by weight and contains a support chosen from the group consisting of activated carbon, alumina, magnesium fluoride and aluminium fluoride; and wherein the fluorine content of the hydrocarbon compound is increased by reacting the hydrocarbon compound with hydrogen fluoride in the gas phase in the presence of the solid composition, the hydrocarbon compound being a saturated halogenated hydrocarbon or an unsaturated halogenated hydrocarbon or an unsaturated hydrocarbon.

8. The process according to claim 7, wherein the solid composition has a specific surface between 1 and 100 m²/g.

9. The process according to claim 1, wherein the component containing chromium oxyfluoride or fluoride is of empirical formula $Cr_xM_{(1-x)}O_rF_s$, where r is greater than or equal to 0 and less than 2.05, s is greater than or equal to [((0.4 r)+1.3)]/0.8, on condition that s is greater than or equal to 1.90 and less than 6.

* * * * *